(12) United States Patent
Desai

(10) Patent No.: US 6,730,081 B1
(45) Date of Patent: May 4, 2004

(54) ENDOSCOPIC SURGICAL INSTRUMENT

(76) Inventor: Ashvin H. Desai, 2195 Trade Zone Blvd., San Jose, CA (US) 95131

( * ) Notice: Subject to any disclaimer, the term of this patent is extended or adjusted under 35 U.S.C. 154(b) by 0 days.

(21) Appl. No.: 08/976,981

(22) Filed: Nov. 24, 1997

Related U.S. Application Data

(63) Continuation-in-part of application No. 08/637,327, filed on Apr. 22, 1996, now Pat. No. 5,976,129, which is a continuation-in-part of application No. 08/259,712, filed on Jun. 14, 1994, now Pat. No. 5,562,703, which is a continuation-in-part of application No. 08/025,003, filed on Mar. 2, 1993, now abandoned, which is a continuation-in-part of application No. 07/779,108, filed on Oct. 18, 1991, now Pat. No. 5,322,503.

(51) Int. Cl.[7] .................................................. A61F 5/00
(52) U.S. Cl. .................................. 606/40; 604/8
(58) Field of Search ........................ 640/6, 7, 8; 606/40

(56) References Cited

U.S. PATENT DOCUMENTS

| | | | |
|---|---|---|---|
| 557,589 A | 7/1896 | Lockwood | 251/349 |
| 1,314,855 A | 9/1919 | Carpenter | 604/33 |
| 2,706,660 A | 4/1955 | Johnson et al. | 251/348 |
| 3,828,780 A | 8/1974 | Morrison | |
| 3,850,175 A | 11/1974 | Inglesias | 606/46 |
| 4,030,480 A | 6/1977 | Meyer | 128/1.5 |
| 4,374,516 A | 2/1983 | Harrison | 128/1.3 |
| 4,402,310 A | 9/1983 | Kimura | 604/30 |
| 4,411,266 A | 10/1983 | Cosman | 128/303.18 |
| 4,565,200 A | 1/1986 | Cosman | 128/642 |
| 4,668,215 A | 5/1987 | Allgood | |
| 4,673,393 A | 6/1987 | Suzuki et al. | 604/167 |
| 4,760,940 A | 8/1988 | Wallace et al. | 251/354 |
| 4,776,840 A | 10/1988 | Freitas | 604/33 |
| 4,895,565 A | 1/1990 | Hillstead | 604/167 |
| 5,007,908 A | 4/1991 | Rydell | 606/47 |
| 5,069,223 A | 12/1991 | McRae | 128/734 |
| 5,071,419 A | 12/1991 | Rydell et al. | 604/35 |
| 5,122,137 A | 6/1992 | Lennox | 606/40 |
| 5,125,910 A | 6/1992 | Freitas | 604/249 |
| 5,186,714 A | 2/1993 | Boudreault et al. | 604/35 |
| 5,188,591 A | 2/1993 | Dorsey, III | 604/249 |
| 5,190,541 A | 3/1993 | Abele et al. | 604/35 |
| 5,195,958 A | 3/1993 | Phillips | 604/33 |
| 5,197,963 A | 3/1993 | Parins | 606/41 |
| 5,219,348 A | 6/1993 | Buess et al. | 606/40 |
| 5,230,704 A | 7/1993 | Moberg et al. | 604/35 |
| 5,244,459 A | 9/1993 | Hill | 604/249 |
| 5,247,966 A | 9/1993 | Stevens et al. | 604/249 |
| 5,273,524 A | 12/1993 | Fox et al. | 604/21 |
| 5,281,218 A | 1/1994 | Imran | 606/41 |
| 5,295,956 A | 3/1994 | Bales et al. | 604/35 |
| 5,370,675 A | 12/1994 | Edwards et al. | 607/101 |
| 5,385,544 A | 1/1995 | Edwards et al. | 604/22 |

FOREIGN PATENT DOCUMENTS

| | | | |
|---|---|---|---|
| EP | 327410 | 8/1989 | |
| WO | WO94/04220 | 3/1994 | A61N/1/06 |

*Primary Examiner*—Michael A. Brown
(74) *Attorney, Agent, or Firm*—David Jaffer; Pillsbury Winthrop LLP

(57) ABSTRACT

An improved electrode for use with an endoscope, used for simultaneously vaporizing, coagulating and cutting of tissue. The construction of the electrodes is such that the connecting end joins an elongated stem having a conductive center conductor, a majority of which is enclosed by a cover constructed from nonconductive material for the purpose of insulating the conductor from the endoscope conduit, telescope and resectoscope sheath. The cover may have an insulated saddle shaped extension for use in guiding a telescope. The conductor divides into two insulated conductive branches, and then exits the insulative cover forming a loop at a distal end of the electrode. The distal end portion of the conductive loop may angle away from the axial direction of the electrode, and the loop is completed with a straight conductive portion upon which an electrode tip is rotatably mounted. Outward conductive tip surfaces have RF energy director points for increasing power density of RF energy coupled thereto from the conductor. The high power density vaporizes surface tissue, and simultaneously coagulates the underlying tissue as well.

28 Claims, 24 Drawing Sheets

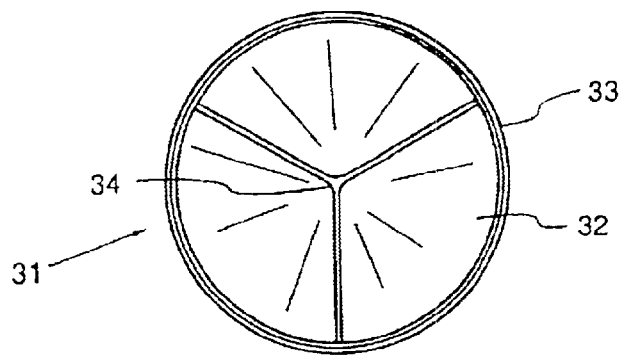 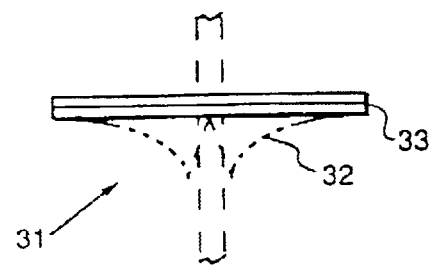
FIG. 3A  FIG. 3B
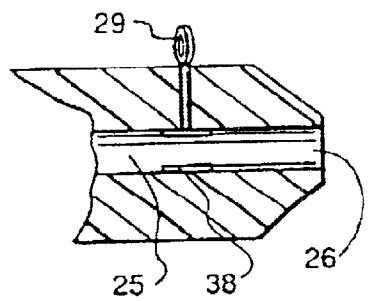 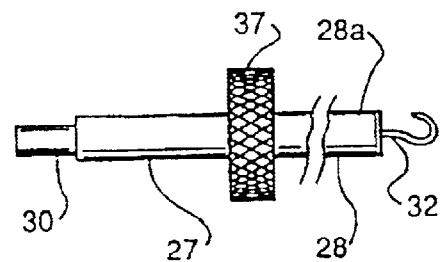
FIG. 4A  FIG. 4B
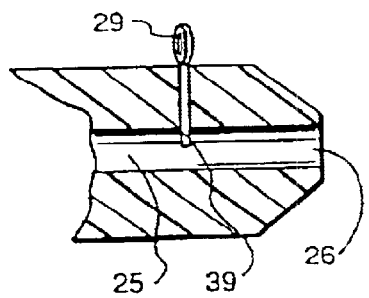 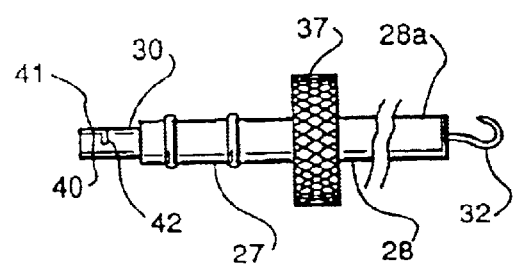
FIG. 5A  FIG. 5B

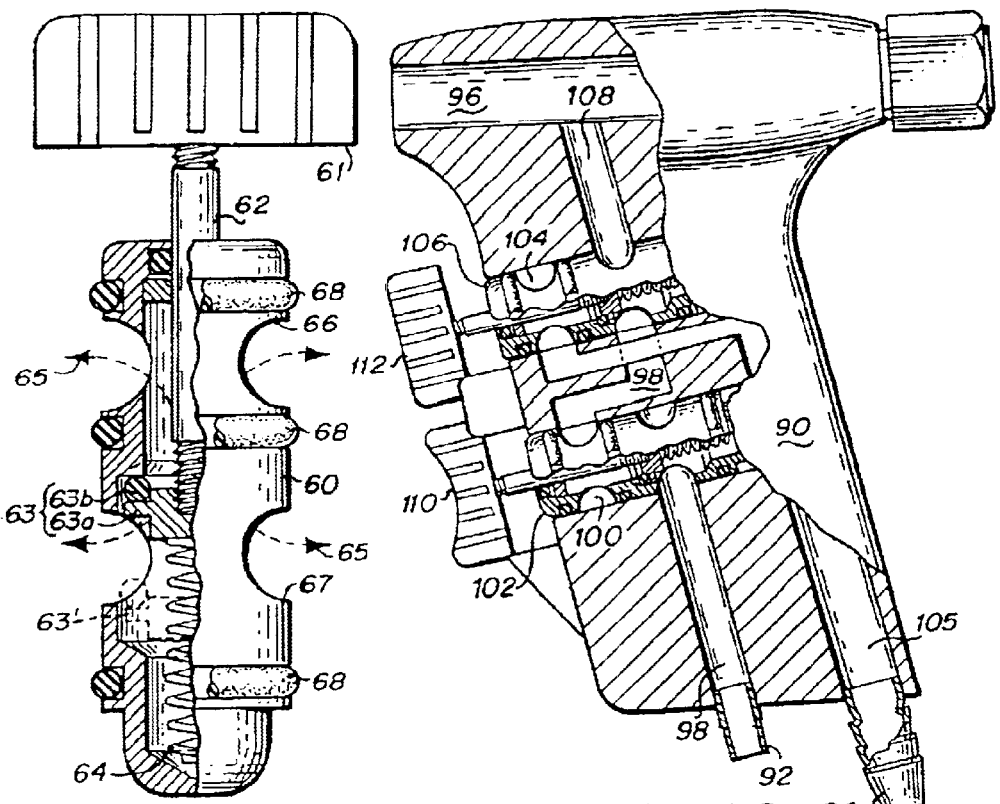
FIG. 9  FIG. 13
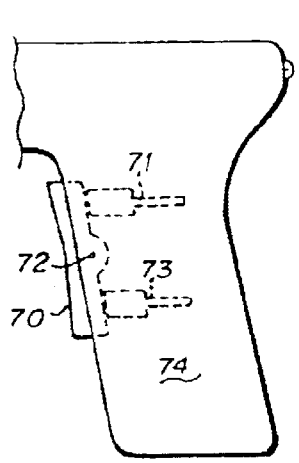
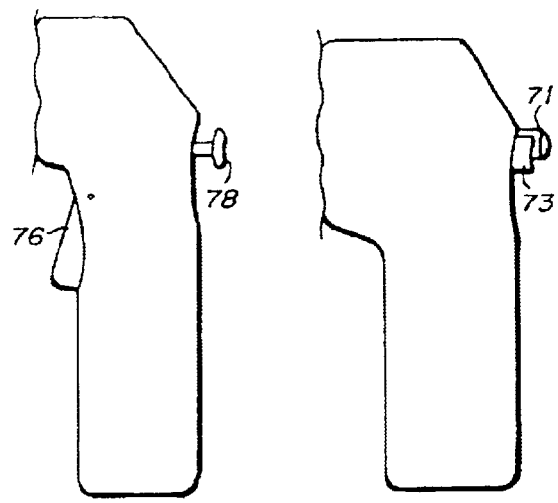
FIG. 10  FIG. 11  FIG. 12

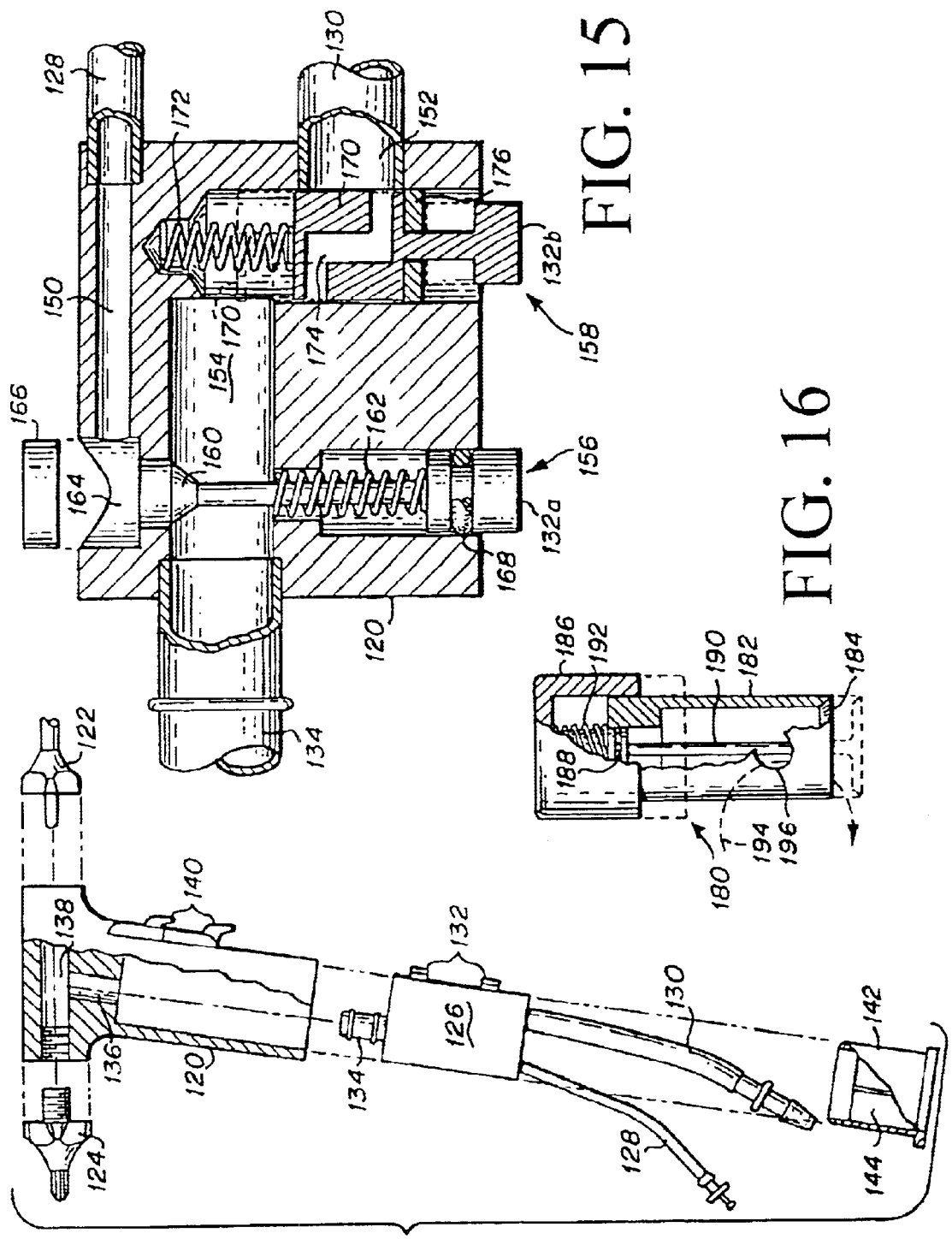

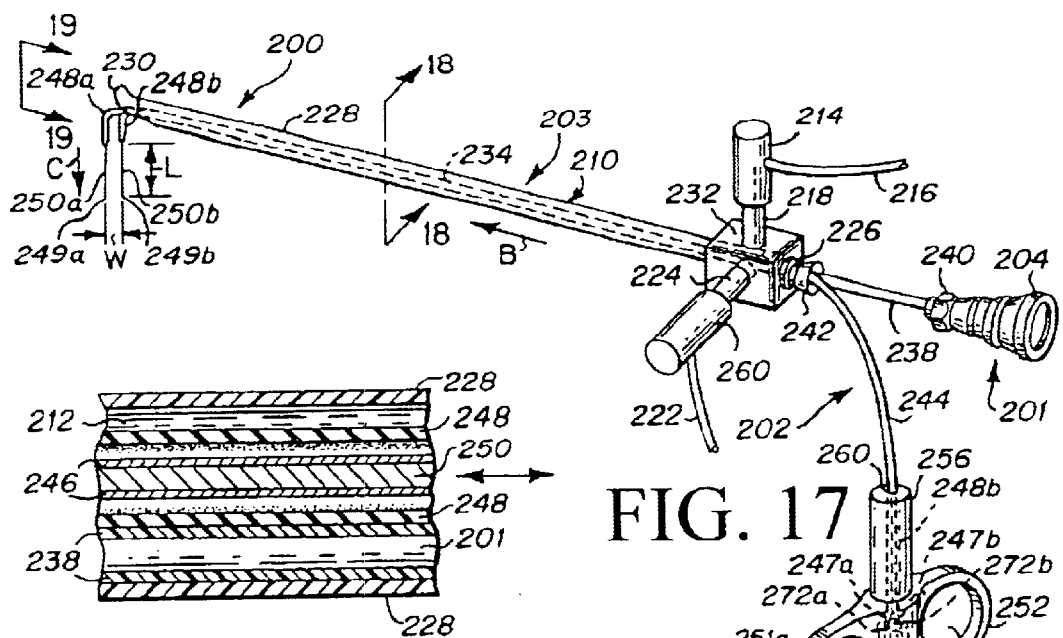
FIG. 17
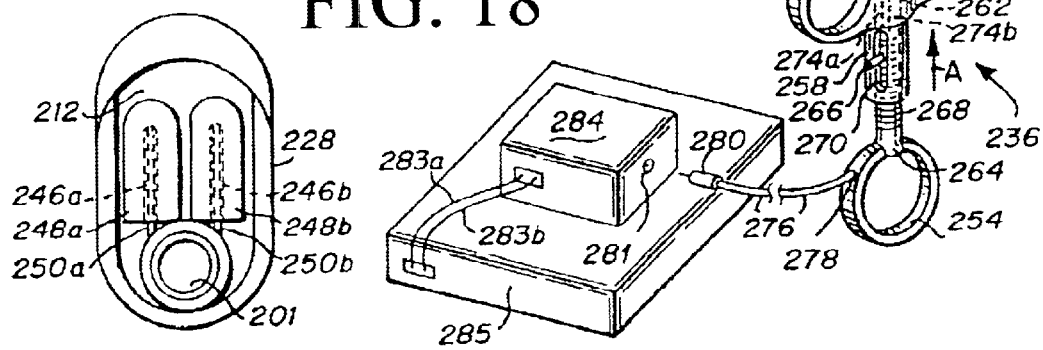
FIG. 18
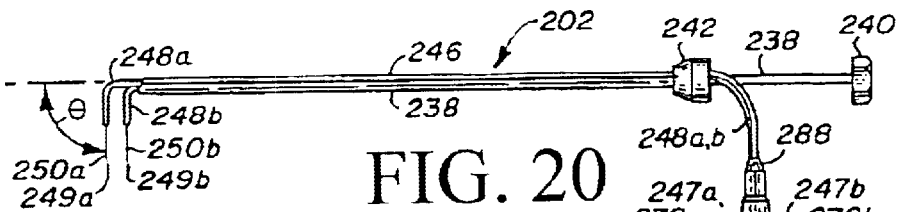
FIG. 19
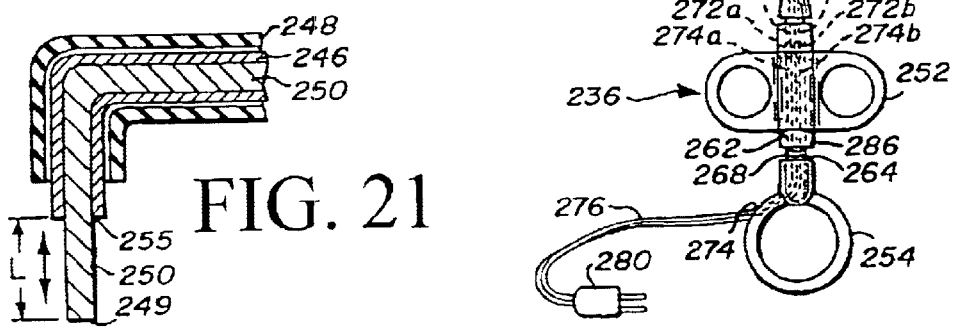
FIG. 20
FIG. 21

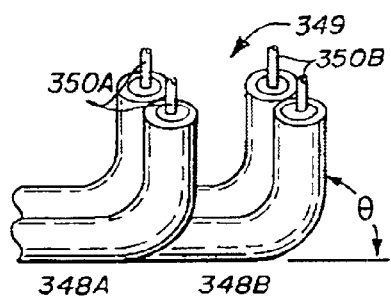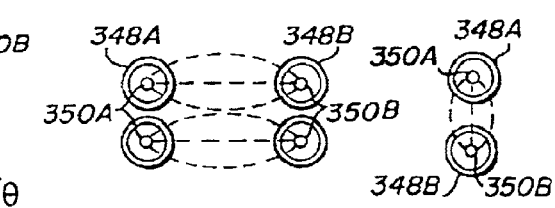
FIG. 25A  FIG. 25B  FIG. 25C
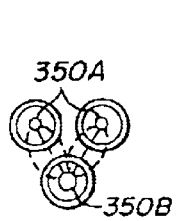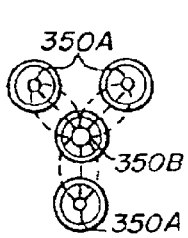
FIG. 25D  FIG. 25E  FIG. 25F
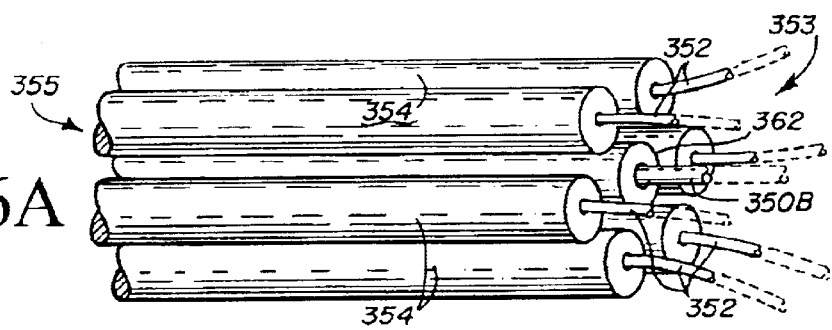
FIG. 26A
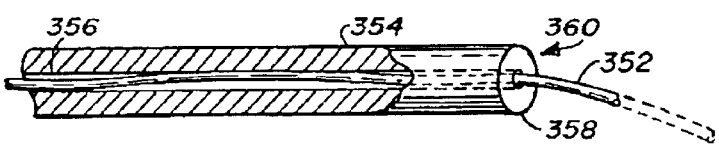
FIG. 26B
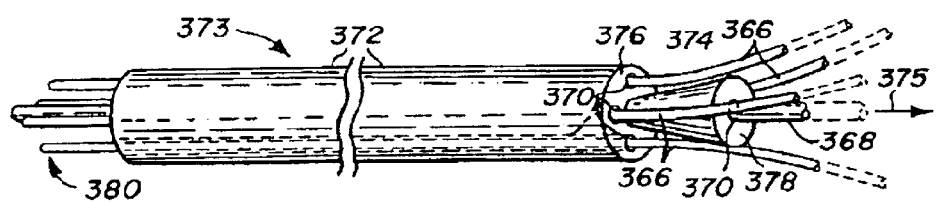
FIG. 27

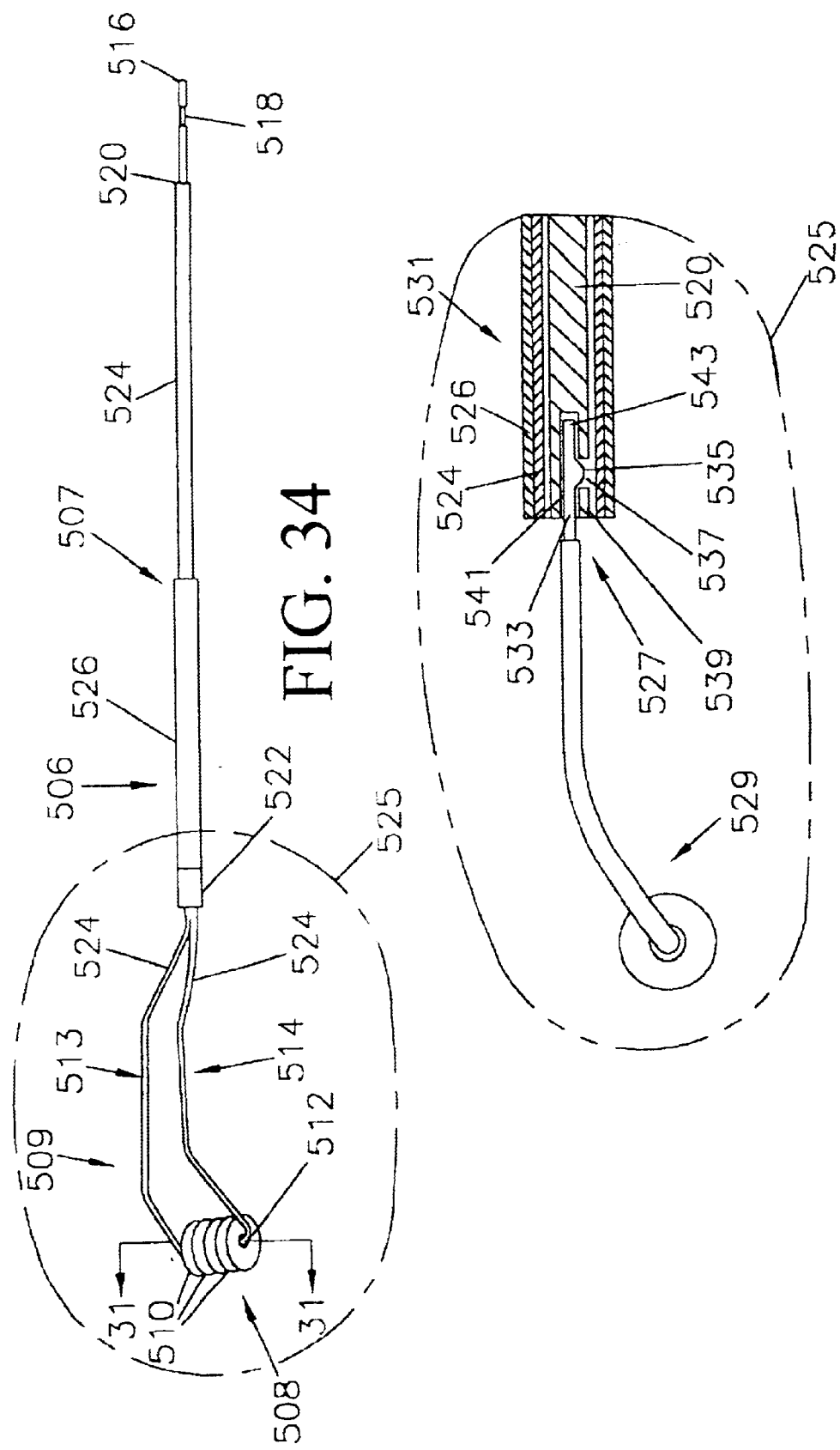

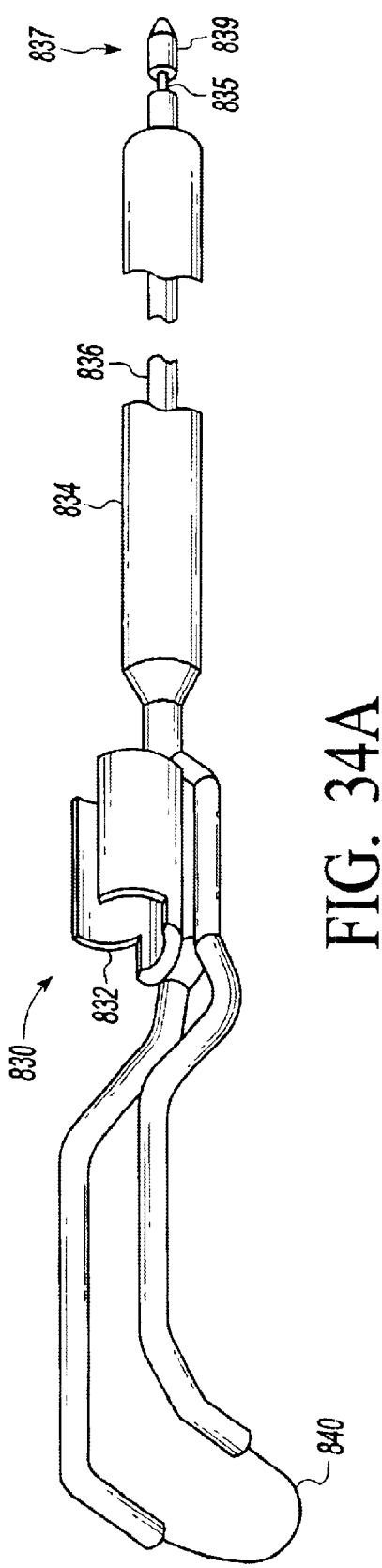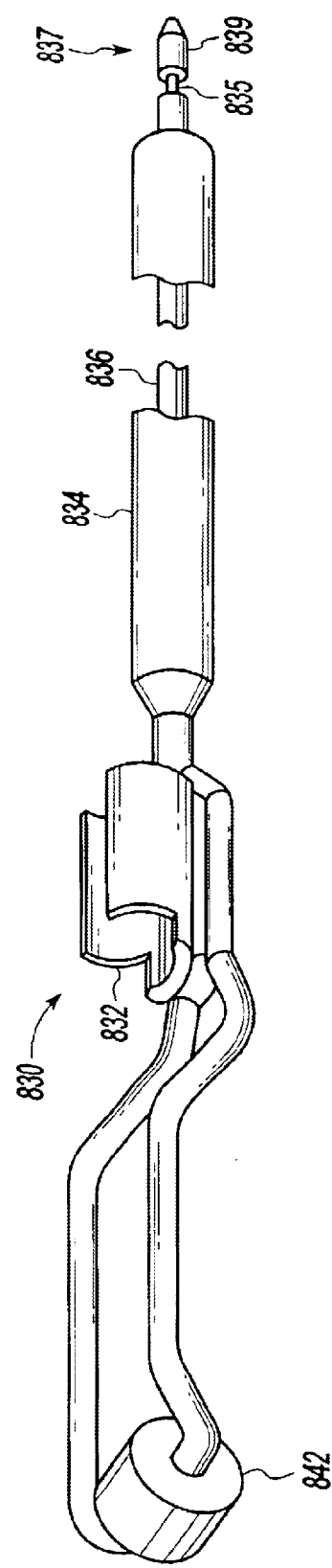
FIG. 34A
FIG. 34B

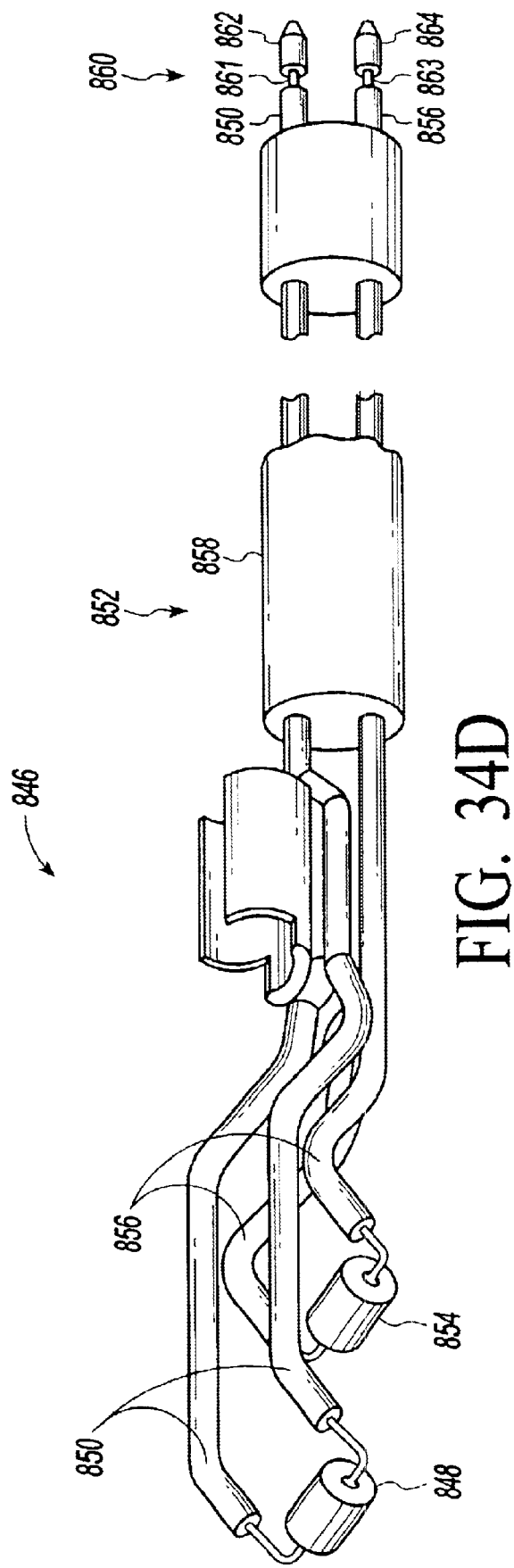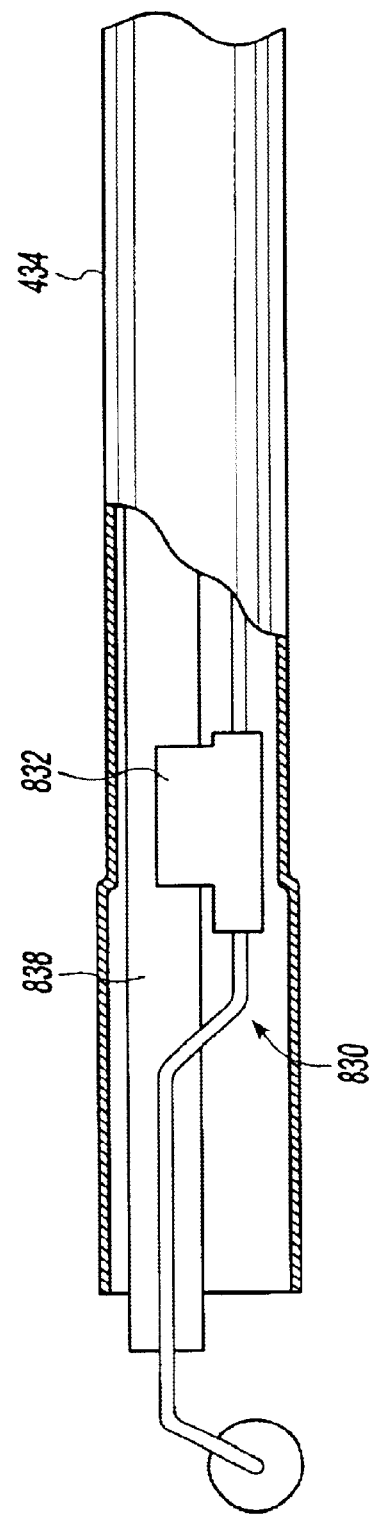
FIG. 34D
FIG. 34E

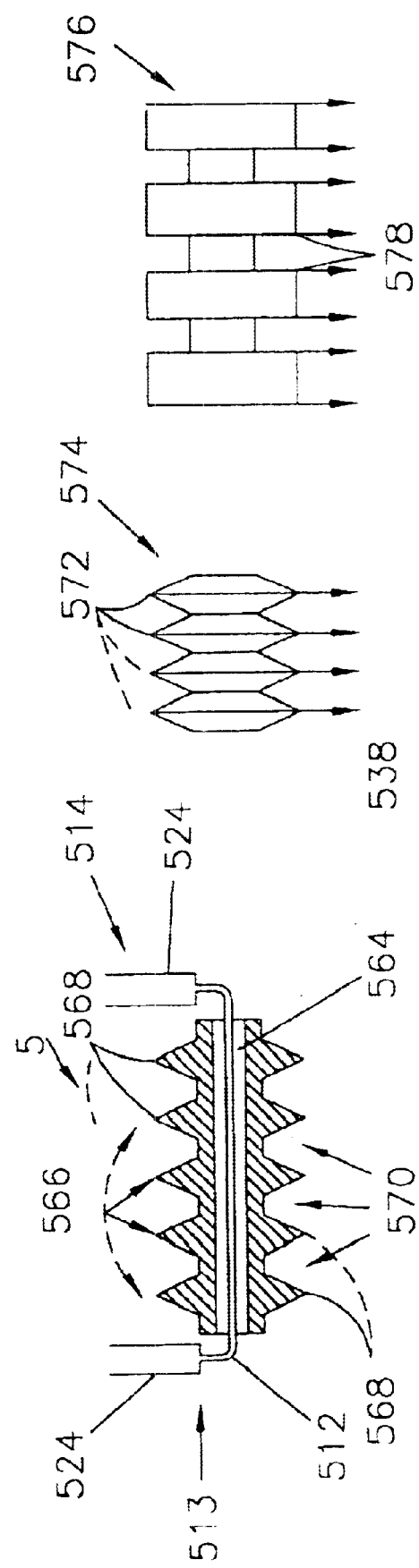

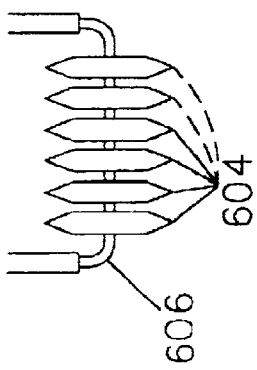
FIG. 45
FIG. 46
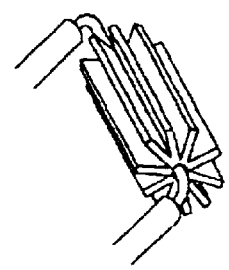
FIG. 47
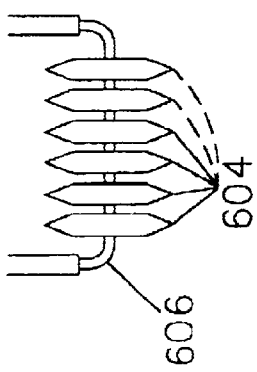
FIG. 48
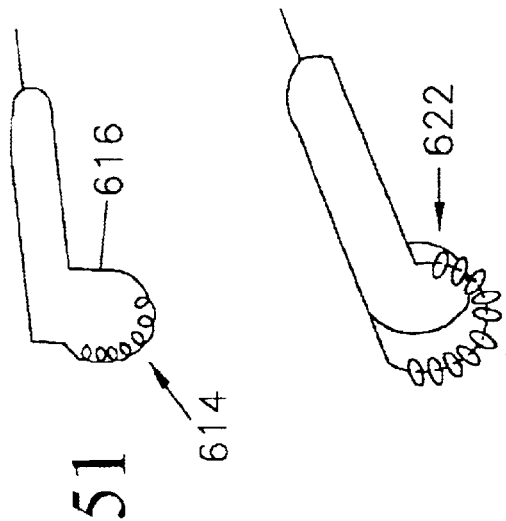
FIG. 51
FIG. 53
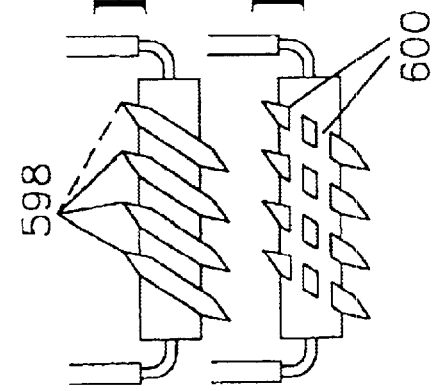
FIG. 50
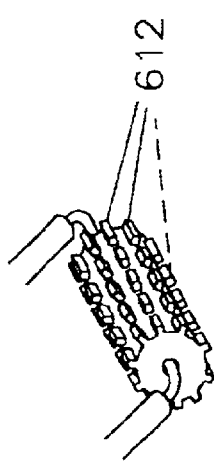
FIG. 52
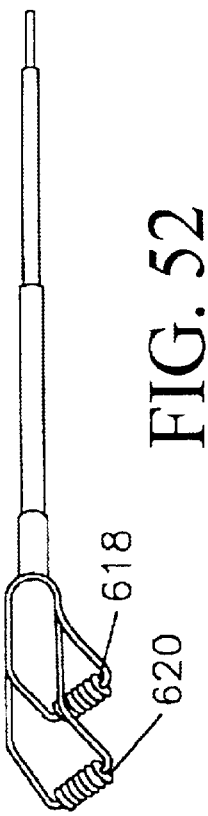

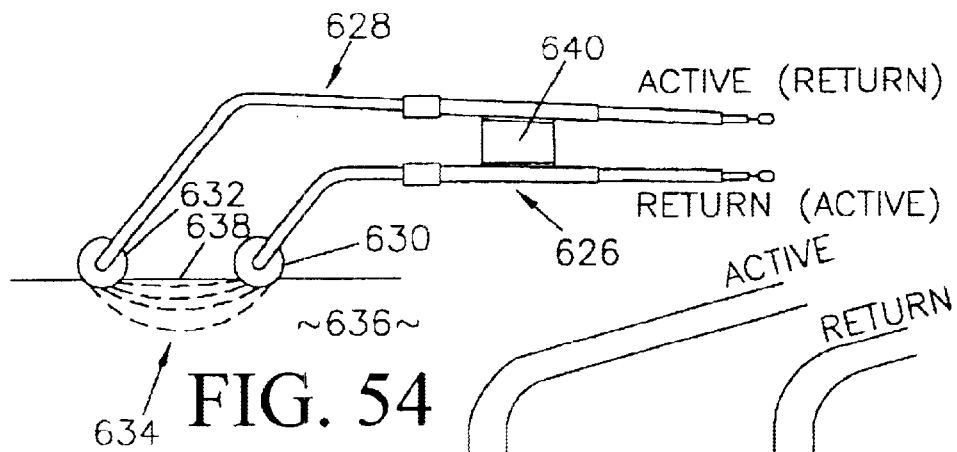
FIG. 54
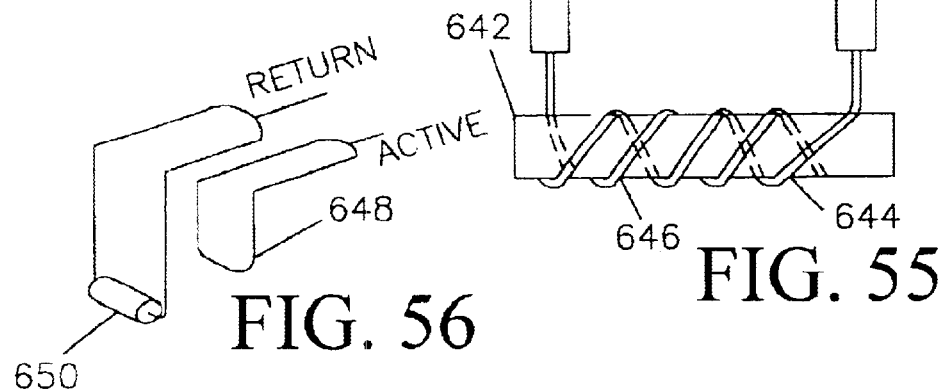
FIG. 55
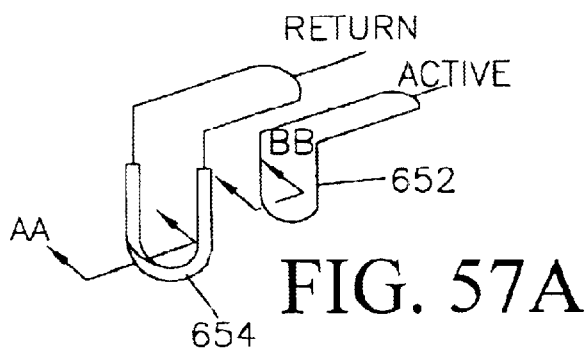
FIG. 56
FIG. 57B
FIG. 57A
  
FIG. 57C  FIG. 57D  FIG. 57E

ENDOSCOPIC SURGICAL INSTRUMENT

RELATED CASES

This application is a continuation-in-part of U.S. patent application Ser. No. 08/637,327 filed Apr. 22, 1996 now U.S. Pat. No. 5,976,129 which is a CIP if 08/259,712 filed Jun. 14, 1994, now U.S. Pat. No. 5,562,703, which is a CIP of 08/025,003 filed Mar. 3, 1993, now abandoned, which is a CIP of 07/779,108 filed Oct. 18, 1991, now U.S. Pat. No. 5,322,503.

BACKGROUND OF THE INVENTION

1. Field of the Invention

This invention relates to a surgical instrument and more particularly to an instrument with the capability for continuous irrigation and evacuation of fluid into and out from a body cavity of a patient during Laparoscopic or Endoscopic surgical procedures, and for the simultaneous measurement of tissue impedance and the ablation of tissue with fixed or retractable electrodes using R.F. energy.

2. Brief Description of the Prior Art

Laparoscopic/endoscopic surgical procedure allows a surgeon to see inside the body cavity of a patient without the necessity of large incisions. This reduces the chances of infection and other complications related to large incisions. The endoscope further allows the surgeon to manipulate microsurgical instruments without impeding the surgeon's view of the area under consideration.

During these surgical procedures it is desirable for as few lines as possible to enter the body of the patient. This reduces the size of the incision the surgeon needs to make. It follows from this that the greater the number of functions provided by a single instrument or the greater the number of instruments able to be passed through a single line entering the patient's body, the better.

Furthermore, in certain procedures it may be desirable to irrigate the area under consideration. This in turn necessitates the evacuation of the irrigation fluid or, when bleeding has occurred, the blood or smoke or tissue residue generated by the surgical procedure.

From what has been said above it should be apparent that it is preferable for both irrigation and evacuation to be conducted along a single conduit which, also, acts as an access line for surgical instruments.

A typical device which is used in endoscopic procedures is an electrosurgical probe. Typically such a probe will comprise a radio frequency (i.e. R.F.) energy conductive tube covered with a dielectric material such as polyolefin or Teflon. At one end, for convenience called the operational end, each probe could have any one of a number of functionally shaped monopolar or bipolar electrodes. In addition a probe could have its end formed specifically for irrigation and/or evacuation.

Monopolar and bipolar electrode probes are known in the prior art. Monopolar electrode probes include a single active electrode which is surgically introduced into a body cavity and engageable with and insertable into a tissue portion of the cavity. A passive electrode is attached to the outer body surface of the patient, e.g. typically a conducting plate is adhesively attached to the patient's leg. The body of the patient serves to complete the electrical circuit. Tissue ablation and coagulation is achieved by introducing sufficient power into the active electrode. Bipolar electrode probes include both active and passive electrodes which are similarly introduced together into the body cavity and are spaced apart from each other by a predetermined distance. Each electrode is engageable with and insertable into the tissue portion. Thus, the electrical circuit is completed by the body tissue disposed between the active and the passive electrodes and only the body tissue disposed between the two electrodes get coagulated.

In surgical operations it is often desirable to remove layers of body tissue. Such an operation can be readily performed if the affected area is totally exposed and large surgical devices can be used. However, large surgical openings are not desirable, due to the resulting bodily trauma, and exposure to the environment which increases the risk of infection. Endoscopic surgery minimizes body trauma and the risk of infection, but the devices of the prior art have significant limitations. FIGS. 29–32 show prior art devices. FIGS. 29–31 illustrate a roller ball, a flat roller bar, and a grooved roller bar respectively. These devices apply RF energy over a significant area and have proven useful for coagulating tissue to reduce bleeding, but they are not useful for tissue vaporization due to low power density. FIG. 32 shows a thin wire loop that concentrates the RF energy and is effective in cutting tissue, but does not function to coagulate, and therefore its use results in significant bleeding which makes it difficult to use in an endoscope due to the time required to remove a cutting electrode and insert a coagulation electrode, and due to the build-up of blood which then needs to be evacuated in order to view the work through the endoscope. There is clearly a need for a surgical device that can remove tissue and simultaneously coagulate the resulting exposed tissue. Use of such a device would leave the surgeon's view unobstructed by blood, and reduce the chance of infection. As a result, more extensive and safer surgery could be performed.

Furthermore, any valves controlling the evacuation and irrigation procedures should be constructed so as to minimize the possibility of the valve malfunctions if, for example, any tissue or blood coagulates around their moving parts. Similarly if any of the instrumentation is to be reusable, such instrumentation, including the valves, should be capable of being efficiently cleaned by, for example, flushing.

U.S. Pat. No. 4,668,215 (Allgood) discloses a valve for switching between an evacuation-and an irrigation conduit and allowing both such evacuation and irrigation to be done via a single line entering the patient. The mechanism for switching between the irrigation, evacuation and closed configurations is by means of a L-valve or T-valve. This patent, in another embodiment thereof, further provides for a piston valve for making an on-off connection between an evacuation port and the line leading into the patient.

The L- and T-valves have the disadvantage that they must be manipulated by rotation by the surgeon, usually using his/her free hand. The piston valve disclosed in this patent has the disadvantage that it has many areas where blood and tissue accumulation and coagulation can occur which may result in the malfunctioning of the valve. In addition, the piston valve has numerous "dead" areas where fluid flow would not occur. This precludes the device from being effectively cleaned by commonly used flushing techniques. Finally, the Allgood patent does not disclose a single body for housing an evacuation/irrigation control valve together with a housing for laparoscopic and microsurgical instrumentation.

A surgical valve that the applicant is aware of is the piston valve illustrated in FIG. 1 of the accompanying drawings.

In this valve a piston 10 is located within a cylinder 11. The piston 10 can be moved along the bore of the cylinder 11 by means of a plunger 12, from a closed position (as shown) to an open position in which a conduit 13 is aligned with an access port 14. This allows fluid flow along a path to or from access port 14, via conduit 13 and space 16 from or to a further port 15. Upon release of the plunger 12 the piston 10 returns to its closed position under action of a spring 17.

This valve, although easy to use, has the disadvantage that blood and tissue accumulation occurs in space 16 and clogs both the space and the spring 17. This may result in undesirable over-evacuation or irrigation of the patient during surgical procedures.

OBJECTS OF THE INVENTION

It is therefore an object of this invention to provide a surgical instrument which includes control means to allow for the continuous irrigation and evacuation of a body cavity of a patient during microsurgical procedures, with both irrigation and evacuation being performed along a single line into the patient. The instrument should also act as a mounting for electrosurgical probes and microsurgical instruments.

A further object of the invention is to provide a configuration for an instrument which, depending on the material it is constructed of, can be both disposable and non-disposable. In the event that the instrument is "reusable" or "reposable" it is an object of the invention to provide the instrument with conduits, access ports and valves which can easily be cleaned by means of commonly used cleaning techniques and conventional sterilization methods.

It is another object of the invention to provide an electrosurgical instrument with fixed or retractable RF electrodes having the capability to simultaneously perform controlled ablation of tissue using monopolar/bipolar R.F. energy and precise measurement of tissue impedance.

An object of the present invention is to provide an adjustable area of tissue coagulation, which may be larger or smaller than the size of the probe enclosing the electrodes. A further object is to provide multiple bipolar electrodes to allow a larger zone of coagulation. The spacing of the multiple electrodes may be adjusted for larger or smaller coagulation zones.

Another object of the present invention is to provide a single connecting cable system for use with an RF energy source and an RF electrode means whereby either the monopolar or bipolar output mode from the energy source may be selected and used with a single RF electrode means. The connecting cable system permits use of the single electrode means for either RF output mode (monopolar or bipolar, which are typically labelled CUT and COAG, respectively on commercially available RF generators), and the user may elect the output mode while the electrode means are in situ.

Still another object of the invention is to provide a method for hysteroscopic and laparoscopic treatment of uterine fibroids/myomas with monopolar or bipolar electrosurgical instrumentation for controlled ablation of tissue.

It is a further object of the present invention to provide an RF electrode for use with an endoscope that can cut and coagulate tissue simultaneously.

It is another object of the invention to provide an RF electrode for use with an endoscope that can vaporize and coagulate tissue simultaneously.

It is a further object of the present invention to provide a method of cutting, coagulating and vaporization of tissue using an isotonic solution to conduct RF energy in monopolar or bipolar operation.

It is a still further object of the present invention to provide an RF electrode having non-conductive material to isolate RF energy from the endoscopic instrument resectoscope, telescope and working element.

It is a still further object of the present invention to provide a bipolar RF electrode for use with an endoscope that can resect, vaporize and coagulate tissue.

SUMMARY OF THE INVENTION

According to this invention, an endoscopic surgical instrument comprises an irrigation and an evacuation port, each port being connected through independent valves to a single access conduit; a probe connector located at one end of the access conduit, the probe connector being for receiving and retaining a hollow surgical probe; and a monopolar or bipolar radio frequency connector which exits into the access conduit in such a manner so as to make radio frequency connection with a probe received by the probe connector.

Preferably the connector for receiving an end, for convenience called the locating end, of the probe would be in the form of a receiving bore in the access conduit which would include a plurality of O-rings which provide a fluid-tight seal around the locating end of the probe. These O-rings also function to retain the probe in the receiving port while allowing the probe to be rotated. In one embodiment of the invention, the O-rings are, instead of being located within the receiving bore of the access conduit, located about the locating end of the probe.

This invention also provides for a valve, for use as either an evacuation or an irrigation valve, the valve comprising a housing, an activator connected to the housing, at least a first and a second valve access conduit, both of which exit into the housing and a fluid impervious seal mounted within the housing such that activation of the activator causes the first valve conduit to move axially relative to the seal and the second valve conduit such that the seal is disengaged and the conduits are placed in direct fluid communication with each other.

Typically, the instrument of the invention would contain two of the above described valves. One valve would act as an evacuator control while the other valve would act as an irrigation control. Both valves communicate into a single access conduit which, when the instrument is in use, continuously flows into the patient via the receiving bore and the hollow interior of the electrostatic probe.

Preferably the endoscopic surgical instrument of the invention is in the form of a pistol with the "barrel" portion thereof having, at one end thereof, the receiving bore for the locating end of the endoscopic probe and, at the other end thereof, the access port for the microsurgical instruments and endoscopes.

The valves for controlling the evacuation and irrigation procedures may be mounted in the "handle" portion of the pistol-shaped instrument. The valves may be mounted alongside one another in the handle portion and may protrude therefrom to allow finger control by the surgeon using the instrument.

In one alternate embodiment of the invention the surgical instrument includes a housing, a single access conduit formed in the housing, an irrigation port and an evacuation port, each port being connected through independent valves to the single access conduit. The single access conduit has a first end, and a second end which is terminated in an aperture formed in the housing. A closure is provided for the aperture. A viewing device, such as an endoscope, is insertable through the aperture and into the single access conduit. The viewing device is of sufficient length such that it is extendable slightly beyond the first end. A retractable electrode assembly is also insertable through the aperture and into the single access conduit, and is of sufficient length such that it, too, is extendable beyond the first end. The retractable electrode assembly, in one embodiment, includes two retractable RF electrodes spaced apart by a predetermined width. Each RF electrode is made from a superelastic material, e.g. typically Nickel-Titanium (NiTi) metal, is sheathed within a guiding sheath, and is slidable within the sheath such that it is extendable beyond and retractable completely within the sheath. Also, each electrode is connected to a mechanism, operable by a surgeon, for moving the electrode within the sheath. Each electrode is extendable beyond its guiding sheath by a variable length and at a predetermined angle from a longitudinal axis of the single access conduit. Further, each electrode is electrically communicative with means for supplying R.F. energy and means for measuring impedance continuously on a realtime basis.

The present invention includes improved electrodes for simultaneously vaporizing, coagulating and cutting of tissue. The electrodes have a connecting end for making contact to an endoscopic device and an RF energy source. In the preferred embodiment, the construction of the electrodes is such that the connecting end joins an elongated stem having a conductive center conductor,sa majority of which is enclosed by a cover constructed from non-conductive material for the purpose of insulating the conductor from the endoscope conduit, telescope and resectoscope sheath. The cover also preferably has a saddle shaped extension, also preferably constructed of non-conductive material, for use in guiding a telescope. The conductor divides into two insulated conductive branches forming a loop at a distal end of the electrode opposite the connecting end. In a preferred embodiment, the distal end portion of the conductive loop angles away from the axial direction of the electrode, and the loop is completed with a straight conductive portion forming an axle for supporting a conductive roller thereon. The outward conductive roller surface has RF energy director points for increasing power density of RF energy coupled thereto from the conductor. The high power density vaporizes surface tissue, and simultaneously coagulates the underlying tissue as well. An alternate embodiment includes a standard loop shaped cutting electrode tip followed by a similarly shaped loop electrode with an enlargened conductor for coagulating the tissue exposed by the cutting tip.

An advantage of the present invention is the provision of an electrode that can both vaporize tissue for removal, and coagulate the underlying tissue to reduce bleeding.

A still further advantage of the present invention is a reduction in operating time because there is no need to change electrodes from a cutting electrode to a coagulating electrode.

Another advantage of the present invention is that it provides an endoscopic surgical instrument having an electrode, operable in either monopolar or bipolar mode, and with or without an isotonic solution allowing improved control over the area and volume of tissue treated, thereby eliminating the need for a conventional patient electrical return pad, reducing damage to surrounding healthy tissue.

These and other objects and advantages of the present invention will no doubt become apparent to those skilled in the art after having read the following detailed description of the preferred embodiment which is illustrated in the several figures of the drawing.

IN THE DRAWINGS

In the following drawings:

FIGS. 3A–3B illustrate a tricuspid valved access port in plan (a) and elevation (b) views;

FIG. 4A is a section through a receiving bore of the instrument illustrating one way of locating a probe in the bore;

FIG. 4B is an illustration of a probe for use with the connector shown in FIG. 4A;

FIG. 5A is a section through a similar receiving bore showing a different way of locating a probe in the bore;

FIG. 5B is an illustration of a probe for use with the connector of FIG. 5A;

FIG. 9 is a partial section through a different type of valve also suitable for use in the instrument of the invention;

FIGS. 10, 11, 12 and 13 are diagrammatic illustrations showing various configurations of valve operating buttons and triggers;

FIG. 14 is an exploded view of an alternative embodiment of the surgical instrument of the invention illustrating a disposable valve cartridge;

FIG. 15 is a cross section through the disposable valve cartridge illustrated in FIG. 14;

FIG. 16 is a partially sectioned view of another type of valve which can be used in the surgical instrument of the invention;

FIG. 17 is a perspective view of an alternate embodiment of the endoscopic surgical instrument having generally similar valves, as illustrated in FIGS. 7–8, and a retractable electrode assembly having bipolar RF electrodes in electrical communication with a R.F. energy source and a tissue impedance monitoring device;

FIG. 18 is a partial sectional view taken along the line 18—18 of FIG. 17;

FIG. 19 is a view taken along the line 19—19 of FIG. 17;

FIG. 20 is a side elevation view of the retractable electrode assembly shown in FIG. 17;

FIG. 21 is an enlarged view of the tip of the retractable electrode assembly shown in FIG. 17;

FIG. 25(*a*) is an illustration of the use of multiple electrodes oriented at an angle theta;

FIG. 25(b) shows an end view of the electrodes of FIG. 25(a) providing a rectangular pattern;

FIG. 25(c) shows a view similar to FIG. 25(b), in which two electrodes are used;

FIG. 25(d) illustrates the use of three electrodes for obtaining an approximate circular coagulation pattern;

FIG. 25(e) illustrates the use of four electrodes to achieve an approximate circular coagulation pattern;

FIG. 25(f) shows the use of nine electrodes to achieve an improved circular pattern;

FIG. 26(a) illustrates the use of superelastic metal electrodes to achieve an adjustable pattern;

Figure 28:
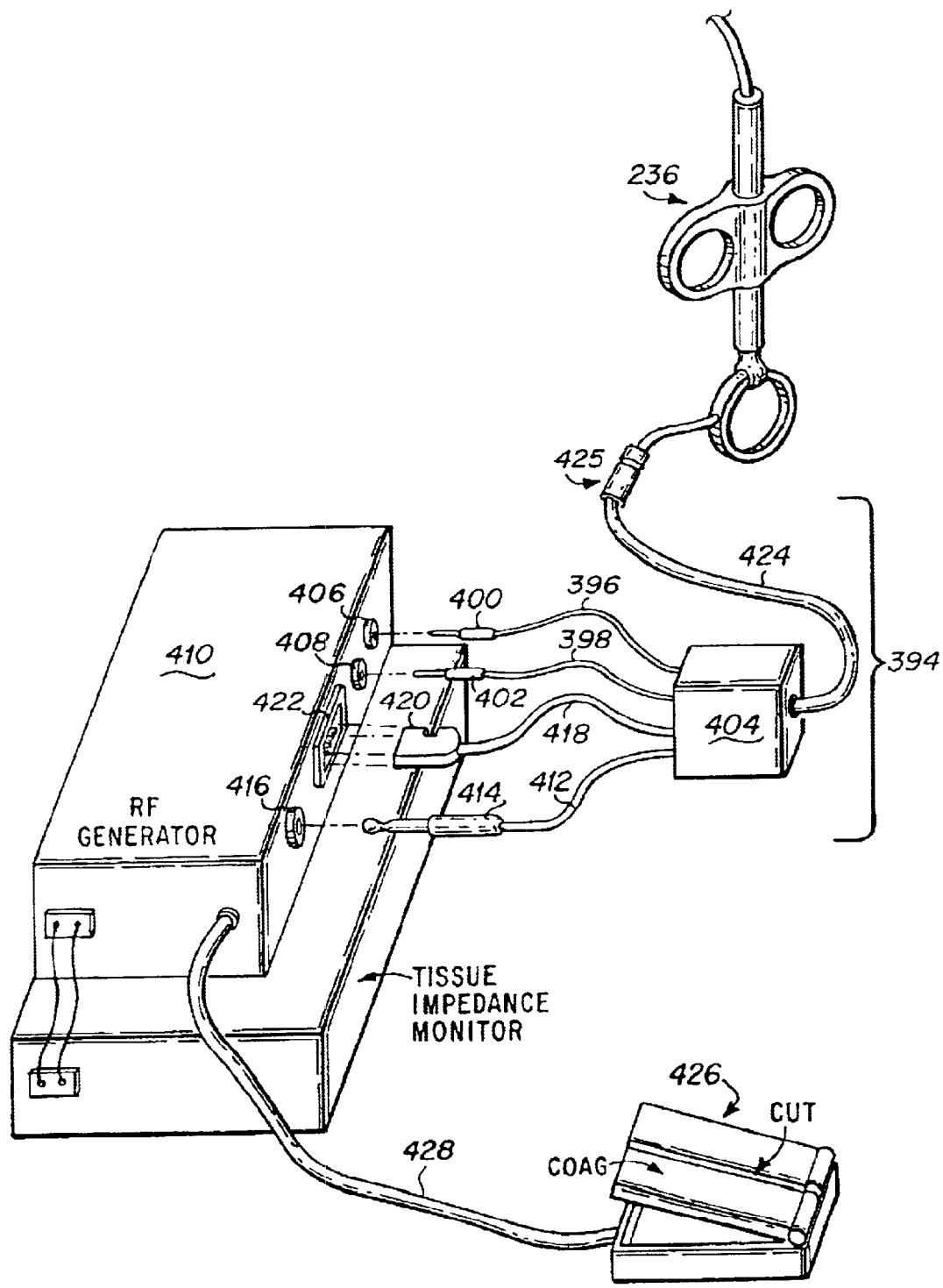
Figure 29:
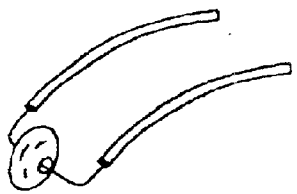
Figure 30:
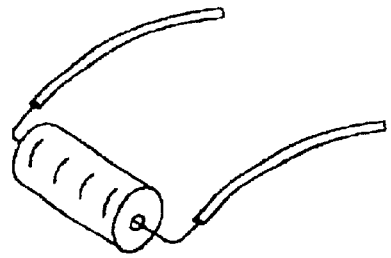
Figure 31:
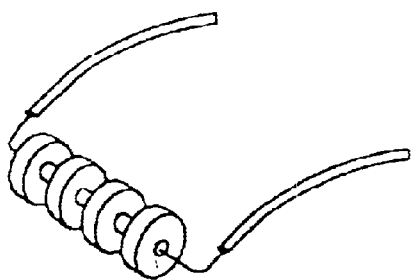
Figure 32:
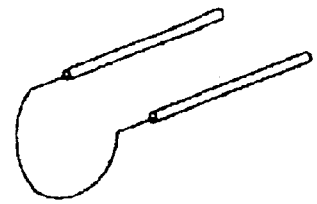

FIG. 26(b) further clarifies the configuration of FIG. 26(a);

FIG. 27 illustrates the use of a frusto-conical extension for deflecting the electrodes to achieve an adjustable zone of coagulation;

FIG. 28 shows a connecting cable system for selectively applying bipolar or monopolar RF power to the electrodes.

Figure 33:
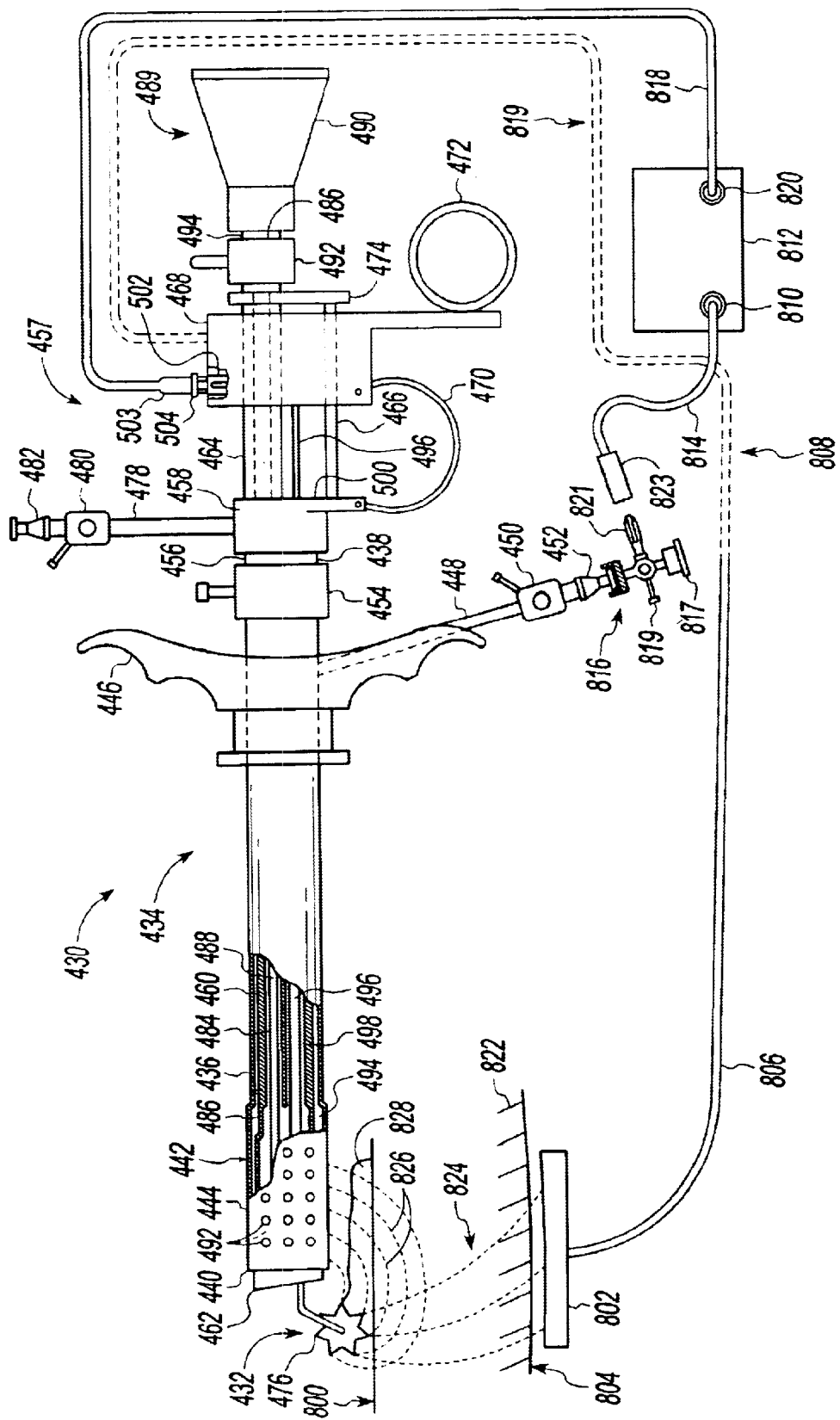
Figure 34C:
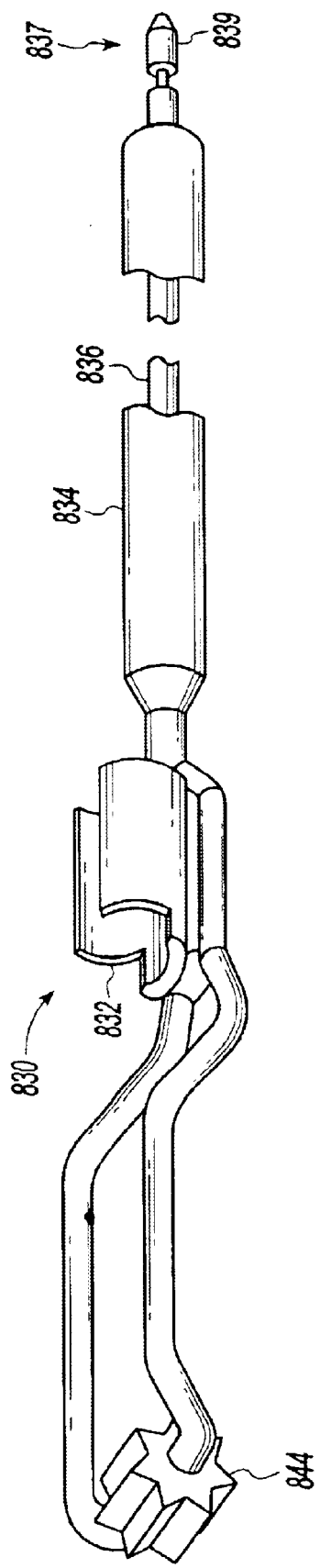
Figure 36:
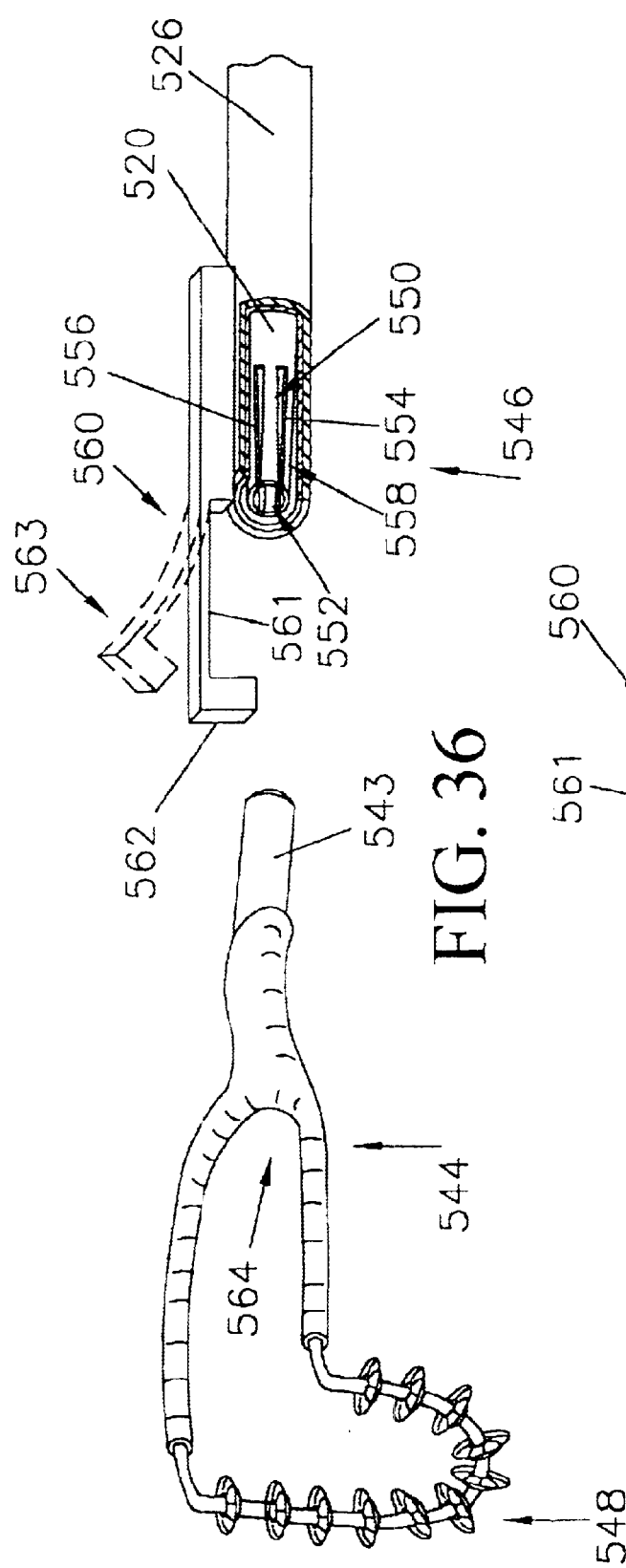
Figure 37:
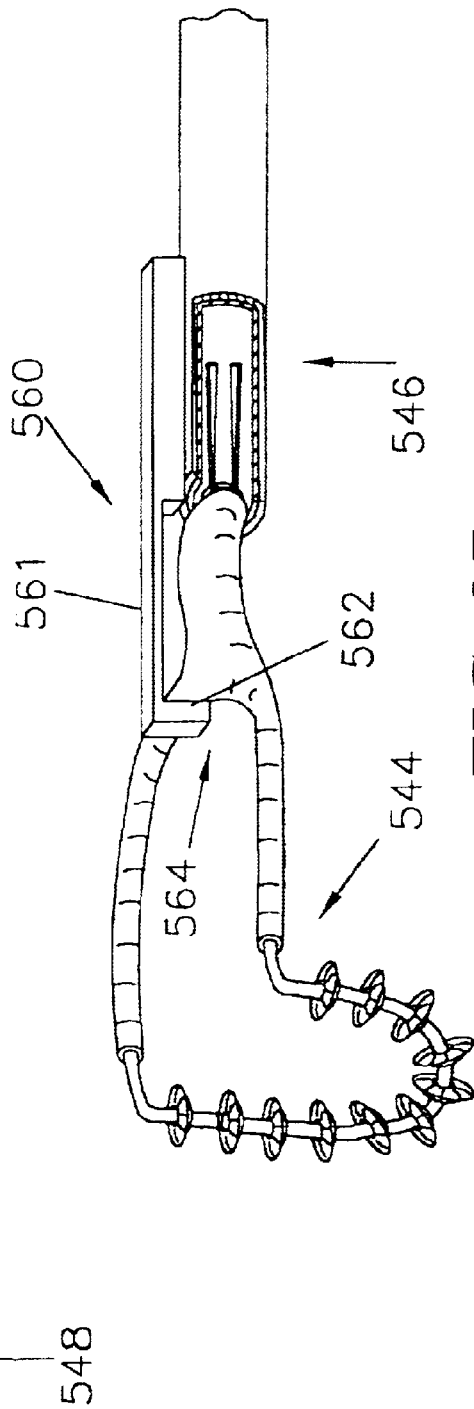
Figure 39:
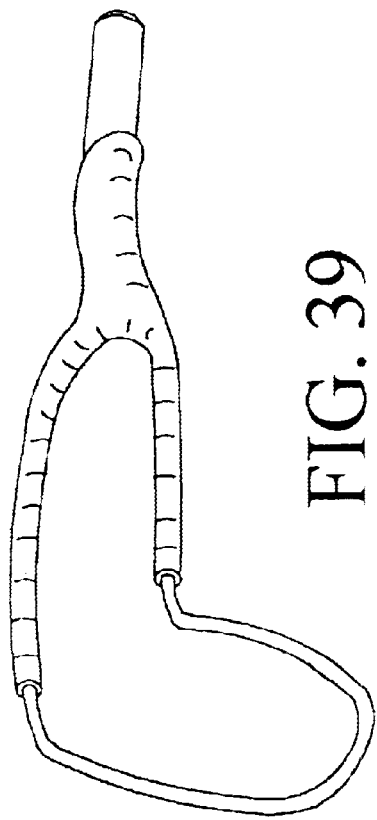
Figure 38:
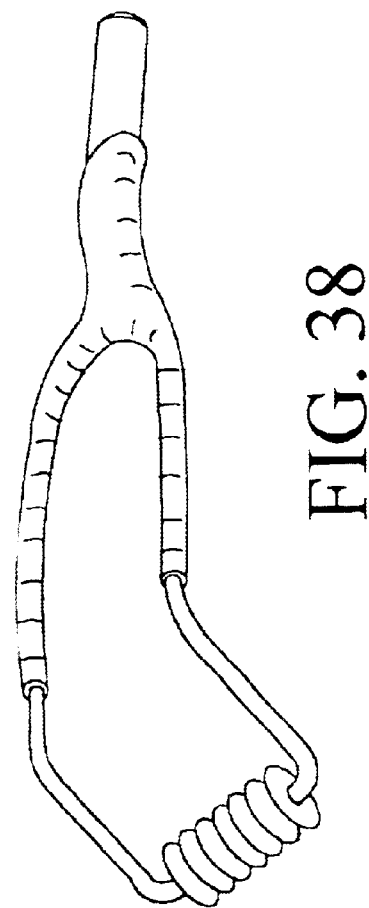
Figure 40:
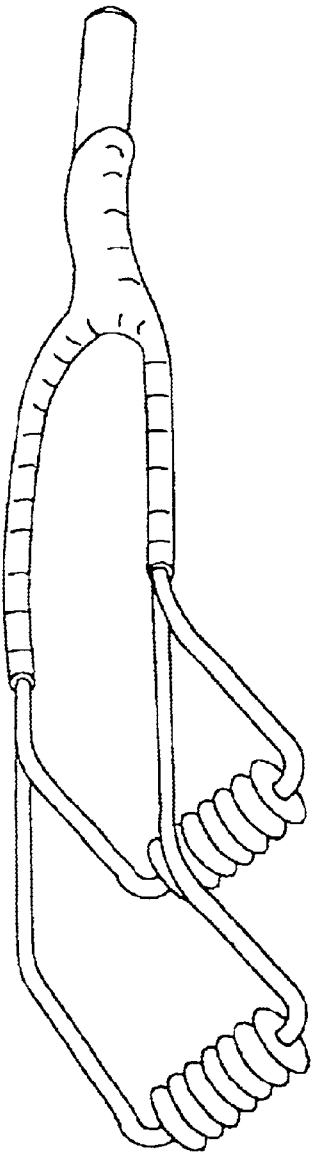
Figure 44:
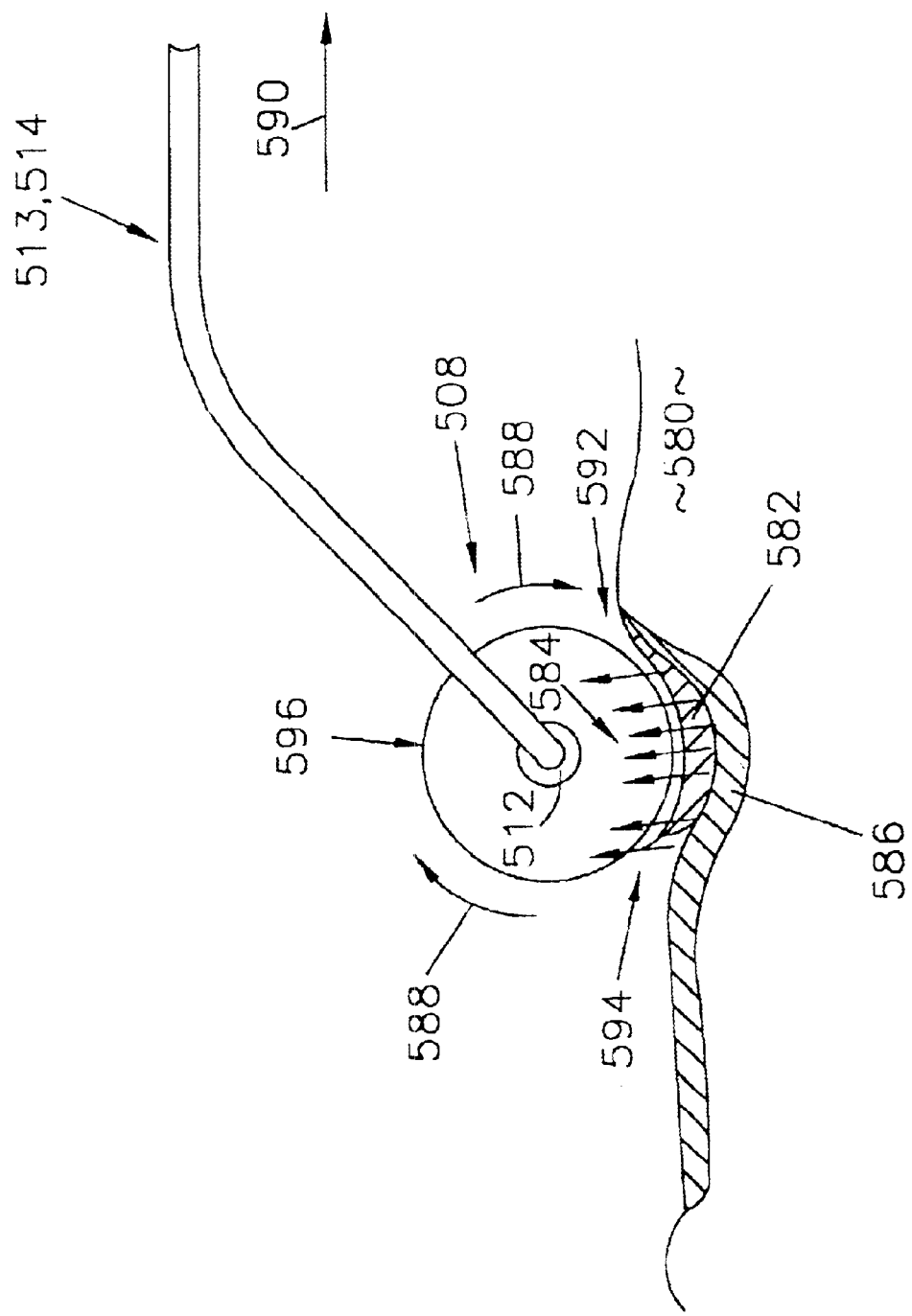
Figure 49A:
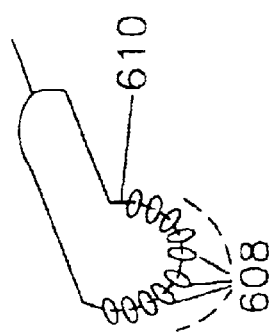
Figure 49B:
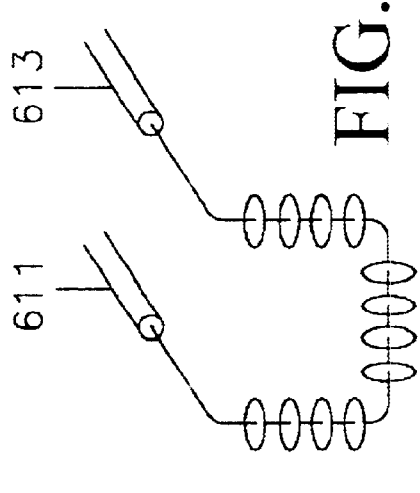
Figure 49C:
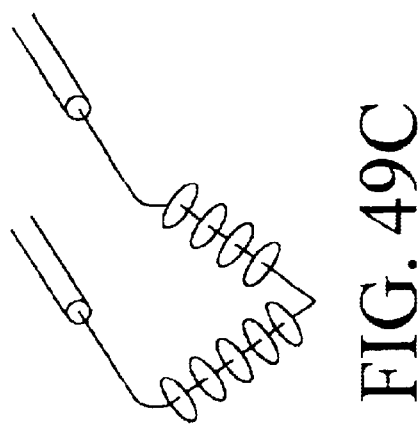
Figure 49D:
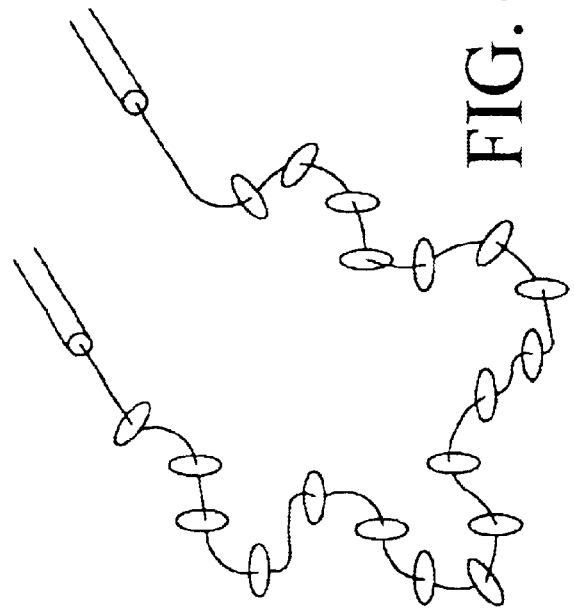
Figure 58:
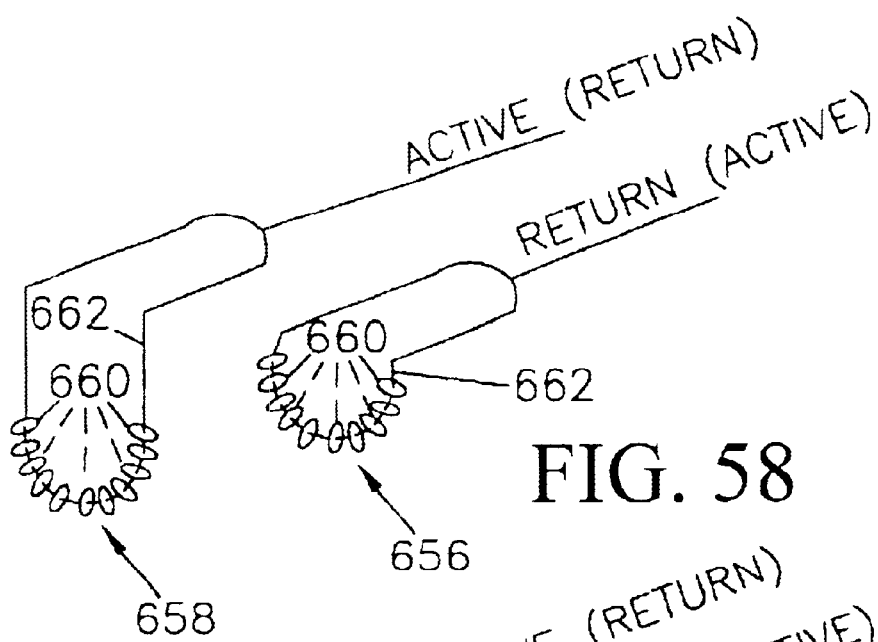
Figure 59:
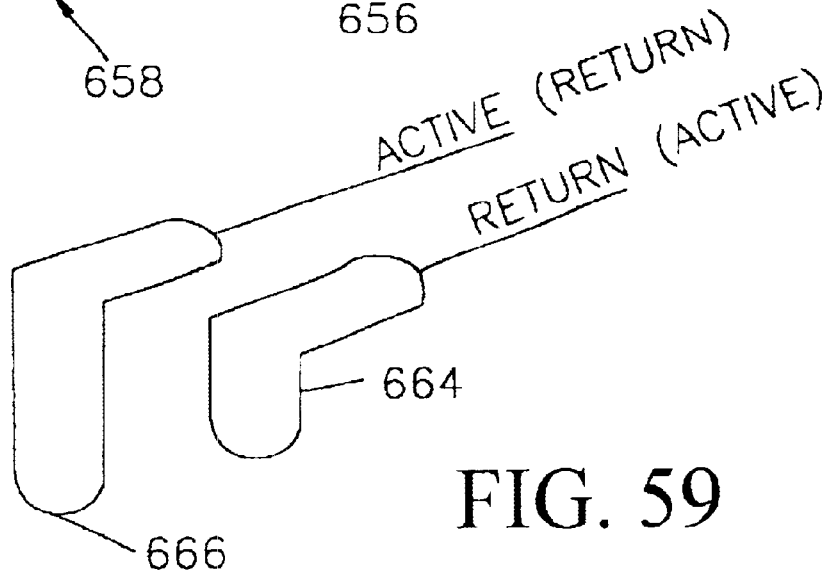
Figure 60:
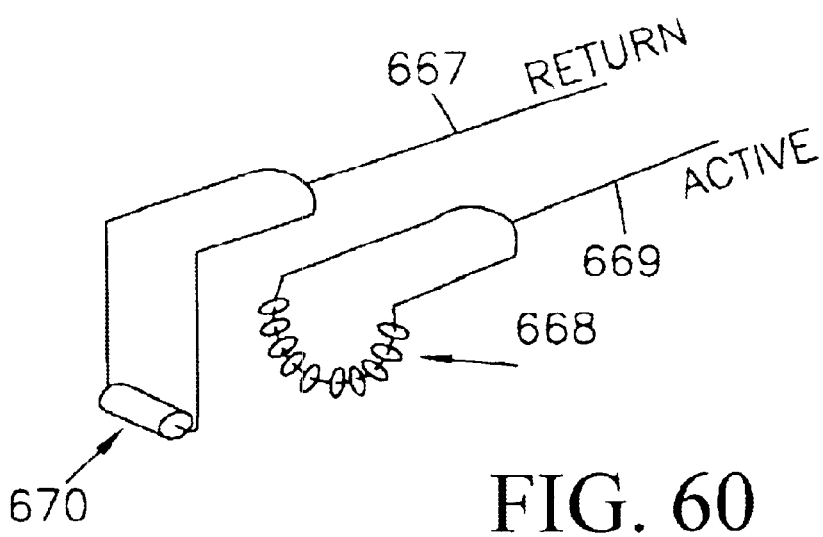
Figure 61:
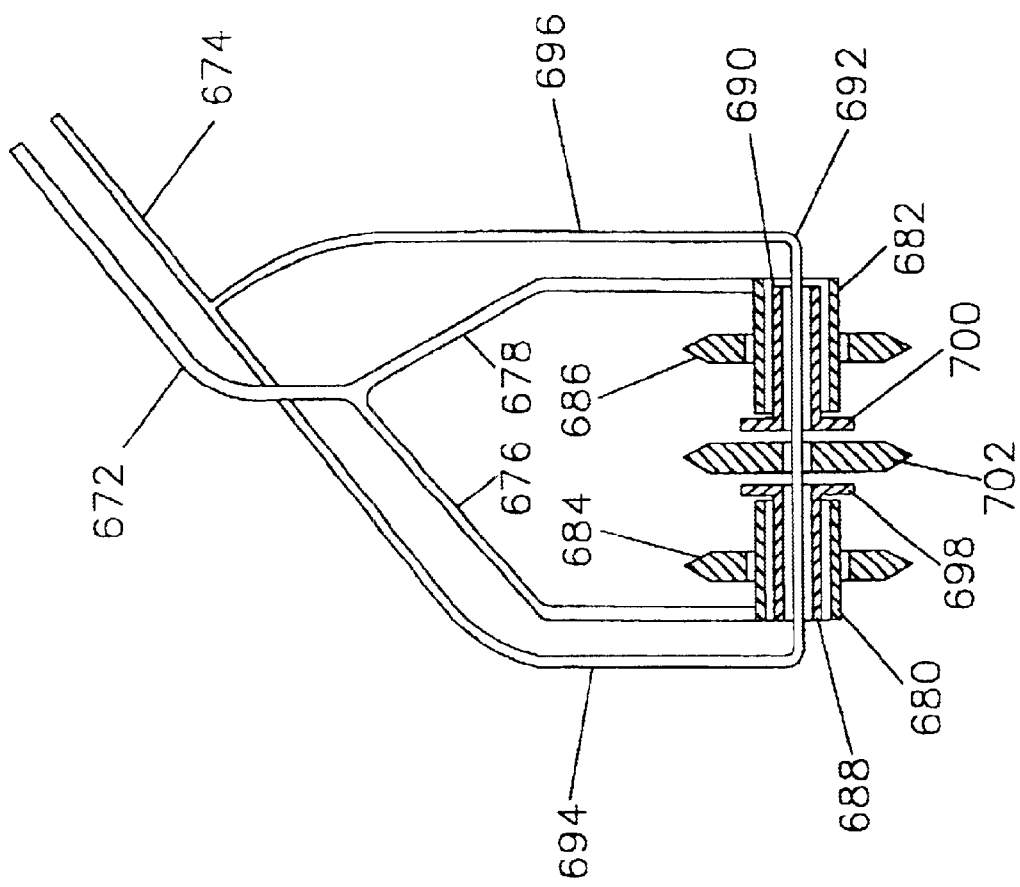

FIGS. 29–32 illustrate prior art RF electrodes;

FIG. 33 shows an alternative style of endoscopic device with electrode movement mechanism;

FIG. 34 shows an electrode with a field enhancement tip;

FIG. 34A shows an insulated electrode with a telescope guide and a cutting loop;

FIG. 34B shows an insulated electrode with a telescope guide and a roller electrode tip;

FIG. 34C shows an insulated electrode with a telescope guide and a field enhancement tip;

FIG. 34D illustrates a dual electrode tip apparatus for bipolar operation;

FIG. 34E shows an insulated electrode with-a telescope guide installed in a probe housing;

FIG. 35 shows a tip module and interconnection with an electrode stem;

FIG. 36 shows an alternate electrode tip module and stem;

FIG. 37 shows the alternate module and stem interconnected;

FIG. 38 shows a roller tip on a tip module;

FIG. 39 shows a cutting loop on a tip module;

FIG. 40 shows two roller tips on a tip module;

FIG. 41 is a cross sectional view of the rotatable mounting of a roller on an electrode conductor;

FIG. 42 illustrates the RF field concentration for a roller with disk-like protrusions;

FIG. 43 illustrates the RF field concentration of a prior art device used for coagulation;

FIG. 44 is an illustration of a roller vaporizing and coagulating tissue;

FIG. 45 shows a roller tip with helical shaped energy directors;

FIG. 46 shows the roller tip with grooves cut across the helical shaped energy directors;

FIG. 47 shows a roller tip having a star configuration;

FIG. 48 illustrates the use of narrow edged disks on an electrode wire;

FIG. 49A shows narrow edged disks on a semicircular shaped electrode conductor;

FIGS. 49B–49D show alternative roller loop electrode configurations;

FIG. 50 is a pictorial view of a roller tip with a plurality of reduced area energy directors;

FIG. 51 illustrates an electrode with a coil wire tip;

FIG. 52 illustrates an electrode using two field enhancement roller bar tips for monopolar operation;

FIG. 53 shows an electrode having a narrow wire electrode and a vaporizing roller loop electrode for monopolar operation;

FIG. 54 illustrates the use of two field enhancement roller bar electrodes for bipolar operation;

FIG. 55 shows two coil electrodes interwound for bipolar operation;

FIG. 56 illustrates the use of a thin wire electrode (active) for connection to the active side of an RF supply for cutting and a roller electrode (return) for connection to the return side of the RF supply for coagulation, in bipolar operation;

FIG. 57A illustrates the use of a thin wire electrode (active) for cutting and a thicker electrode (return) for coagulation for bipolar operation;

FIGS. 57B–57E illustrate various electrode cross section shapes;

FIG. 58 shows two vaporizing roller loop electrodes illustrating the independent disks on semicircular wires, arranged for bipolar operation;

FIG. 59 shows two thin wire electrodes in a bipolar configuration;

FIG. 60 illustrates a roller loop vaporizing electrode with independent disks in combination with a roller electrode for bipolar operation; and FIG. 61 illustrates an integrated bipolar electrode using roller disks.

DETAILED DESCRIPTION OF PREFERRED EMBODIMENTS

Figure 1:
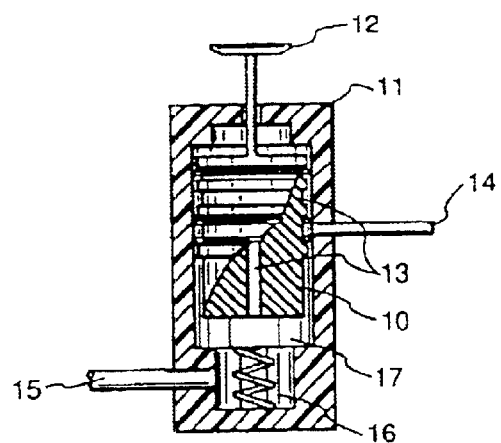
FIG. 1 is a partial sectional elevation through a prior art piston valve.
Figure 2:
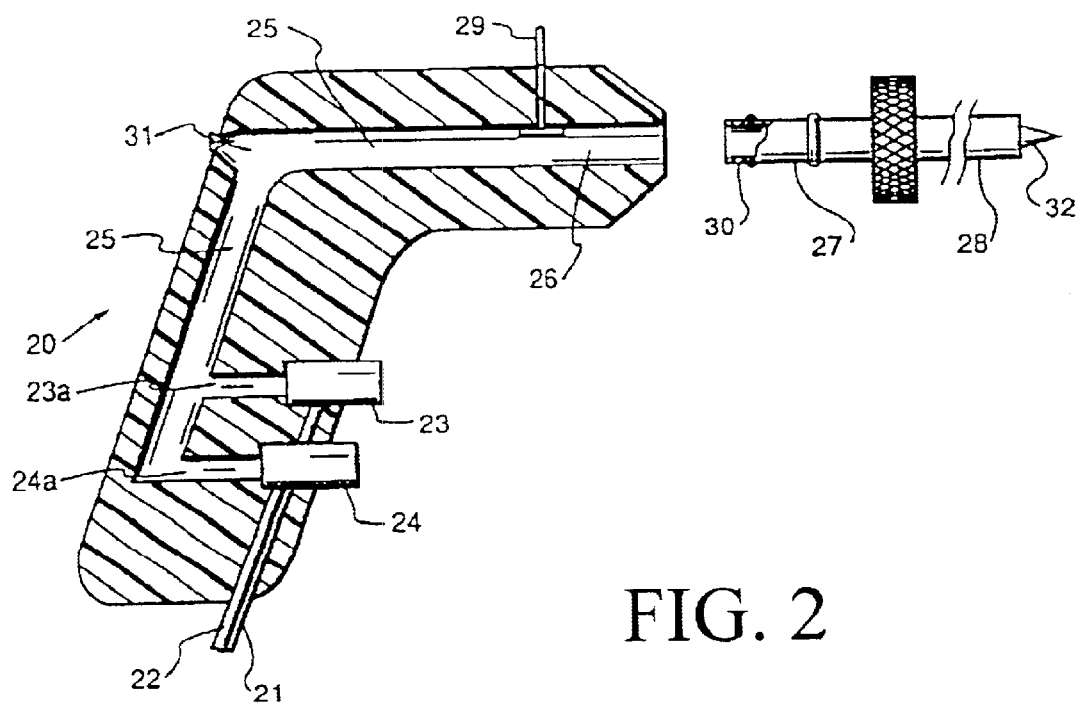
FIG. 2 is a diagrammatic section through a semi-exploded elevation of one embodiment of the endoscopic surgical instrument of the invention.

In FIG. 2 of the accompanying drawings, the endoscopic surgical instrument of the invention is generally indicated as 20. The instrument 20 is shown to include an irrigation port 21 and an evacuation port 22. Each port, 21 and 22, is connected through independent valves 23 and 24, respectively, to a single access conduit 25. The connection between the valves 23 and 24 and conduit 25 is along connector tubes 23a and 24a.

The access conduit 25 leads from the valves and their respective valve conduits to a probe connector 26. This probe connector 26 is designed to receive one end, the locating end 27, of a surgical probe 28 which would be used during microsurgical procedures. The connection 26 is described in more detail with reference to FIGS. 4 and 5 hereafter.

At or near the probe connector 26, a monopolar/bipolar radio frequency connector 29 is located. As illustrated, this is in the form of a R.F. connector. The advantage of a R.F. connector is that it is an industry standard and can be used for connecting the instrument 20 to standard R.F. energy sources marketed by a number of different manufacturers.

The radio frequency connector 29 exits into the access conduit 25 where it makes connection with a point 30, on the locating end 27 of a probe 28 received by the probe connector 26.

The surgical instrument 20 also includes a port 31 which allows the surgeon to insert microsurgical instrumentation and viewing devices along the access conduit 25 and the bore of the hollow probe 28 to exit from the end 32 thereof. The port 31 should provide a fluid-tight seal when no microsurgical instrumentation is being used with the surgical instrument 20. This will prevent fluid, which may be moving along the access conduit 25 to or from the patient, from leaking.

Typically, the access port 31 is in the form of a commercially available tricuspid valve as illustrated in FIGS. 3(a) and (b). In these figures, the valve 31 is shown as being constituted by three segments. 32 which in plan view are wedge-shaped and which together form the disc shaped sealing portion of the valve. The segments 32 are held together by means of a circumferential ring 33 which biases the three segments 32 together to form a fluid-tight seal. In use, the microsurgical instrumentation are inserted through the valve at a point 34 where the apexes of the segments 32 come together. This insertion forces the elements of the valve apart to allow ingress of the microsurgical instrumentation. The effect thereof is shown in broken lines in FIG. 3(b). When the instrumentation is removed from the valve 31, the segments 32 are pulled together to form the seal.

In FIG. 4 the probe connector 26 is shown to be constituted by a receiving bore which is coaxial with the fluid access conduit 25. In practice, the diameter of this bore would be the same as that of the access conduit 25 and would be sized to receive the locating end 27 of the probe 28 in a relatively close fit. Within the bore forming the probe connector, a plurality, typically two, O-rings 36 are located. When the locating end 27 is inserted into the bore 26 these O-rings provide a snug, fluid-tight seal about the end 27. Once the locating end 27 of the probe is received within the bore 26 it is capable of being rotated about its longitudinal axis, by means of a knurled rotation knob 37 located between the locating end 27 and the operational end 32 of the probe 28.

The probe 28 would typically be made of a electrostatic conductive material coated with a non-conductive material such as heat shrink polyolefin or Teflon. Electrostatic/radio frequency energy is passed along the probe 28 from the radio frequency connector 29 via electrostatically conductive plates 38 located within the bore of the probe connector 26 and onto the end 30 of the probe 28. The end 30 is so designed such that when the locating end 27 of the probe is received by the probe connector 26, electrostatic connection is made between the plate 38 and the connector 30. This allows the surgeon to pass energy into the patient being operated on.

An alternative radio frequency connector is illustrated in FIG. 5. In this case, the R.F. connector 29 exits into the bore in the form of a pin 39. In the conductive end 30 of the probe an L-shaped slot 40 is formed. As the probe 28 is inserted into the receiving bore 26, the pin 39 engages the axially-orientated leg 41 of the L-shaped slot 40. When the probe can be inserted no further along the bore it is twisted, in this case in an anti-clockwise direction, such that the pin 39 and the axially transverse leg 42 of the L-shaped slot 40 engage each other to lock the probe 28 into position. In this embodiment the probe 28 cannot be rotated by means of the knurled knob 37.

FIG. 5 further illustrates an alternative positioning of the O-rings 36. In this case they are located on the locating end 27 of the probe 28.

From FIGS. 4 and 5, although not shown, it will be apparent that the diameter of the operational shank 28a of the probe 28 can be variable. Typically, the probe, as shown, would have a diameter of 5 mm. This diameter can, however, be increased to 10 mm which would be close to the diameter of the locating end 27 of the probe, as well as that of the internal bore diameter of the access conduit 25. The advantage of 10 mm diameter probes is that the evacuation of removed tissue and objects such as the gall-stones can be more effectively achieved. Obviously, when the bore of the operating shank 28a of the probe, the locating end 27 and the access conduit 25 are all 10 mm in diameter, the diameter of the evacuation port 22 and its related valve 24 and connector tube 24a must also be 10 mm.

In FIG. 6(a) to (i), a side view of number of different electrode shapes are illustrated. It will be appreciated that the electrode tips could be either monopolar or bipolar. In the case of bipolar electrodes, only one electrode is illustrated since a second electrode is fully obscured by the visible electrode. These electrode tips would be located on the operating end of the probe 28.

As can be seen from the figure, a number of the tips are not symmetrical about the longitudinal axis of the probe 28. It is for this reason that it is desirable for the probe 28 to be mounted on the instrument in such a manner to allow for a rotation of the probe about its longitudinal axis. As has been previously indicated, this will give the surgeon the opportunity of rotating any non-symmetrical tips, inside the patient, without having to rotate his or her wrist.

Figure 6:
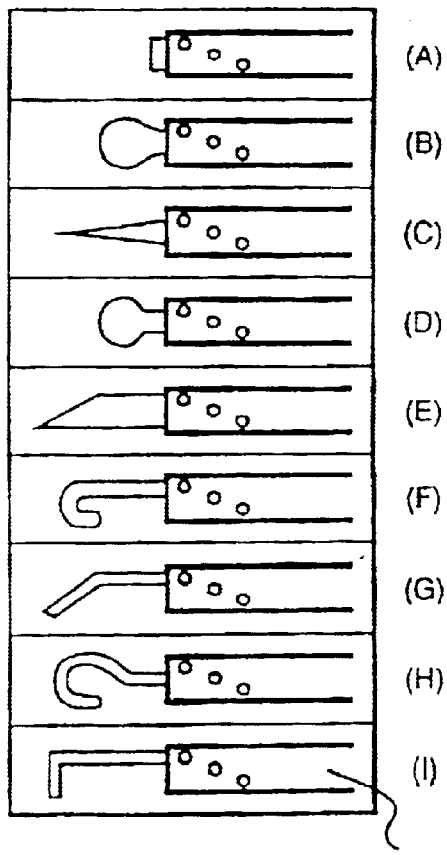
FIG. 6 is a side view illustrating in (a)–(i) various electrostatic probe operational ends.
Figure 22:
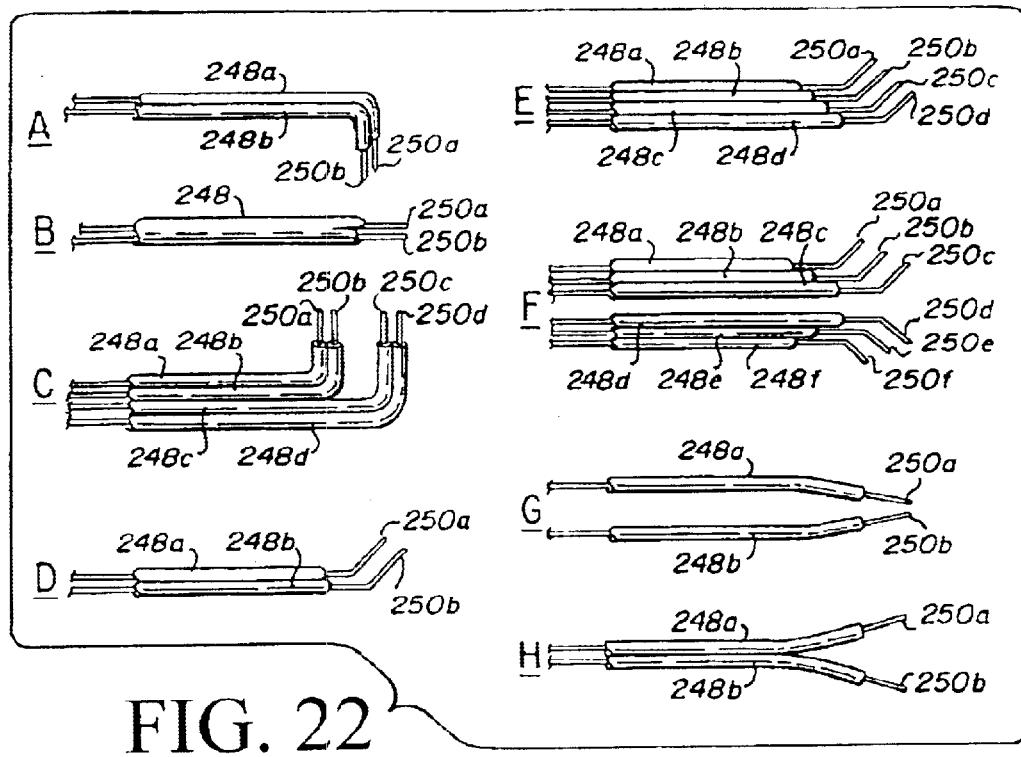
FIGS. 22A–22H illustrate alternate electrode configurations for the retractable electrode assembly shown in FIG. 17 and 20.

This invention extends also to an electrostatic probe 28, substantially as described in any of the FIGS. 4 to 6.

Figure 7:
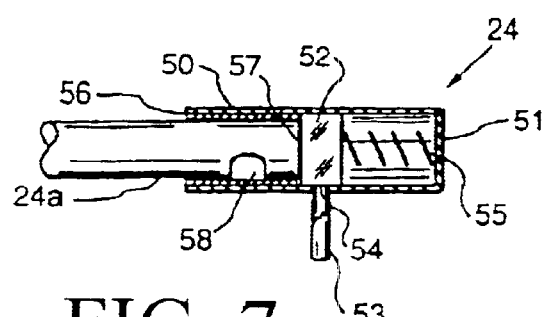
FIG. 7 is a section through a valve according to the invention with the valve being in the shut position.
Figure 8:
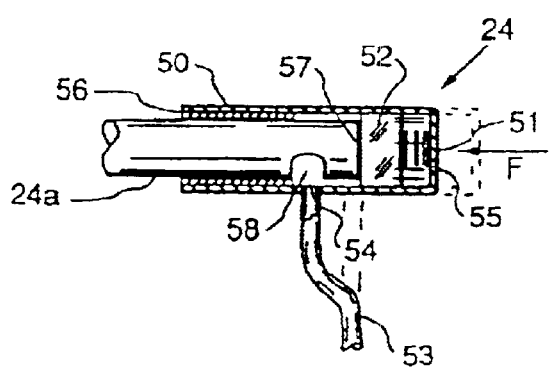
FIG. 8 is the valve of FIG. 7 in the open position.

The details of one type of irrigation/evacuation valve are illustrated in FIGS. 7 and 8. The valve 24 indicated in both figures comprises a housing constituted by a hollow tube 50 and an activator in the form of a button 51 formed integrally with the tube 50. A fluid impervious seal 52 is located within the tube 50. Referring specifically to FIG. 7, in which the valve is shown in the shut position, it can be seen that the seal 52 lies between a first valve conduit 53 which leads to the evacuation port 22 (not shown) and a second valve conduit in the form of connector tube 24a which leads into the primary access conduit 25 of the surgical instrument. In effect, the seal 52 prevents the conduits 53 and 24a from being in communication with each other.

The first valve conduit 53 is mounted onto the wall of the tube 50 and opens into the interior of the tube 50 through a hole 54. Between the seal 52 and the button portion 51 of a tube 50, a spring 55 is located. On the side of the seal 52, opposite to which the spring is located, a tubular insert 56 is located. This tubular insert has a snug but slidable fit over the outer wall of the second valve conduit 24a as well as a tight, fluid impervious fit into the inner bore of the tube 50. This tube 56 acts as a stop which prevents the spring 55 from pushing the seal 52 out of the hollow tube 50.

To open the valve, as is illustrated in FIG. 8, an activating force, applied along a line F to the button 51, will cause the button to move from the position indicated in broken lines to the illustrated open-valve position. As the button moves, so does the hollow tube 50, taking the first valve conduit 53 along with it. In addition, the leading edge 57 of the second valve conduit 24a bears against the seal 52 causing the seal to move relatively to the tube 50. This in turn disengages the seal from sealing the hole 54 in the wall of the tube 50. The movement of the first valve conduit 53, relative to the second valve conduit 24a, places the respective openings 54 and 58 of these two conduits in fluid communication with each other thereby allowing an unobstructed fluid flow along both access conduits.

Upon release of the force on the button 51, the bias of the spring 55 will return the valve to its shut position.

It is evident from the construction of the valves illustrated in FIGS. 7 and 8 that they can be readily cleaned by commonly used cleaning such as flushing. In addition, the valves have almost no areas where blood and tissue accumulation and coagulation can occur, and if such accumulation and coagulation does occur the valves cannot be jammed in the open position. This is because the spring biasing the valve into its closed position is located in an effectively sealed area. Furthermore these valves have been tested to a pressure of up to 100 psi without the integrity of the valve seal being adversely affected.

An alternative form of valve, to that illustrated in FIGS. 7 and 8 above, is shown in FIG. 9. In the figure the valve is shown to include a generally cylindrical valve body 60, an activating button 61 and a plunger 62. A hollow bore runs down the center of the valve body 60 and contains the valve seal 63. The valve seal 63 is made up of a circular washer 63a and a sealing O-ring 63b and is screwed onto the bottom of plunger 62. The valve seal 63 is biased into its illustrated sealing position by means of a spring 64 located in the bottom part of the valve body 60.

To open the valve, the button 61 is depressed so that the plunger 62 forces the valve seal 63 downwards against the bias of the spring 64 to a position shown in broken lines 63', in the figure. As a result, a fluid path, indicated by arrows 65, is opened between an upper pair of cutouts 66 and a lower pair of cutouts 67. Each pair of cutouts opens into the hollow bore in the center of the valve body 60 and, when this valve is inserted into the surgical instrument, into either an evacuation or irrigation conduit. Closure of the valve is achieved by releasing the button and allowing the spring 64 to return the valve seal 63 to the sealing position.

One advantage of this embodiment of the valve is that it is easily removed from and inserted into the surgical instrument of the invention. Accordingly the valve can easily be removed for cleaning or disposal and replacement. This is further illustrated below with respect to FIG. 13. It is sufficient here to mention only that the surgical instrument is provided with a receiving bore for each valve and that the valve includes a plurality (in this case 3) O-rings 68 which, when the valve is inserted into its respective receiving bore, provide a number of fluid tight seals against the inside of the bore.

Either of the two types of valve described in FIGS. 7 to 9 can be used on the instrument 10. Typically one valve would act as an evacuation valve while the other as an irrigation valve. Different types of arrangements of valves and valve activation means are illustrated in the following 4 figures.

One way of activating the valve is by means of a rocker-shaped trigger 70 illustrated in FIG. 10. The trigger 70 is pivotally mounted on a point 72 on the handle. 74 of the pistol. Depressing the trigger 70 to operate the irrigation valve 71 would not interfere with the operation of the evacuation valve 73. Similarly, operation of the trigger 70 to operate the evacuation valve 73 would in no way effect the operation of the irrigation valve.

In FIG. 11 a trigger mechanism 76 is shown for operation of only one of the buttons. The other button 78 would be located for operation by means of the surgeon's thumb in a position removed from the trigger 76. This could, for example, be near the top end of the handle portion of the instrument.

Yet a further positioning of the buttons 71 and 73 is indicated in FIG. 12. In this instance, the buttons protrude from the top rear of the pistol handle and are located side-byside. To prevent confusion between evacuation and irrigation procedures, the tops of the buttons have different shapes. So, for example, the button to manipulate the evacuation valve could be concave while the button for manipulating the irrigation valve could be convexly shaped.

FIG. 13 illustrates still another arrangement of buttons and valves, in this case an arrangement particularly suited to the valve shown in FIG. 9.

In this figure only the pistol grip 90 of the surgical instrument of the invention is shown. An irrigation port 92 and evacuation port 94 enter the pistol grip 90 at the bottom of its handle portion. The ports 92, 94 are, in use, respectively connected to irrigation and evacuation conduits (not shown) and, to this end, suitable connectors, as illustrated, are provided.

The irrigation port 93 communicates with the main access conduit 96 (referenced as 25 in FIGS. 2, 4 and 5) along an irrigation conduit 98 which extends from the irrigation port 93 and into the rear of the bore 100 which houses an irrigation valve 102. From there it extends along the bore 100 to a point near the front of the bore from where it exits into the body of the grip 900 to enter rear of the bore 104 which houses an evacuation valve 106. the irrigation conduit extends directly across the bore 104 at this point and becomes-a central conduit 108 which communicates with the access conduit.

On the other hand, the evacuation port 94 communicates with an evacuation conduit 105 which extends along the pistol grip 90 directly into the front of the bore 104, down to the bore 104 to its rear from where it exits into the central conduit 108.

In the position shown, both the irrigation and evacuation valves 102, 106 respectively, are shown in the off or shut configurations and neither evacuation or irrigation can take place. Should irrigation of the patient be required, the dish-shaped irrigation button 110 is depressed and the valve 102 opens (ie. its valve seat moves to the right in the drawing) to allow irrigation fluid to pass along the irrigation conduit 98 and into the bore 104. In this bore 104 the evacuation valve 106 is in the off configuration. However, a fluid path exists across the pair of cutouts (67 in FIG. 9) and therefore the irrigation fluid can pass through the body of the valve 106 and into the central conduit 108 and, from there, into the access conduit 96.

When evacuation is desired the irrigation button 110 is released and the spring associated with the irrigation valve 102 biases it into the shut or off configuration. Thereafter the flat topped evacuation button 112 is depressed to open the evacuation valve 106. This allows the patient to be evacuated along the main access conduit 96, into the central conduit 108, then from the rear to the front of the bore 104 and, from there, out along the evacuation conduit 105.

As has been indicated earlier, the valves 102, 106 are easily inserted into and removed from their respective bores 100, 104. This allows the pistol grip 90 (which is typically stainless steel and is reusable) to be cleaned efficiently. The valves, typically being of plastic and being difficult to clean, can be discarded and replaced with new valves.

A variation on this theme of discardable valves is illustrated in FIG. 14. In this figure the surgical instrument is shown to include a pistol grip 120, a surgical probe 122, which can be screwed into the front of the pistol grip 120 and a radio frequency connector 124 which screws into the back of the grip 120.

The instrument also includes a removable (and disposable) valve cartridge 126. The cartridge 126 includes an irrigation pipe 128 and an evacuation pipe 130 both of which are individually operated by valves (as will be further illustrated in FIG. 15) under action of button-shaped actuators 132. Both the irrigation and evacuation pipes communicate into a single conduit (not shown) which runs down the center of a male connector fitting 134. Where the cartridge 126 is inserted into the grip 120 the connector 134 fits into the base of a central conduit 136 which, in turn, opens up into the main access conduit 138 of the instrument. When the cartridge 126 is located in the grip 120 the actuators 132 are located directly below a pair of operating triggers 140 which can be used to operate the irrigation/evacuation procedures described before.

Finally, when the cartridge 126 is in place, it is held there by means of a retainer clip 142 which clips in behind the cartridge 126. The retainer clip 142 has apertures 144 formed in it to allow the irrigation and evacuation pipes 128, 130 to pass through it.

Although it will be apparent that the valve types described above are also suitable for use in the cartridge 126, a further valve configuration is illustrated in FIG. 15, which illustrates the cartridge 126 in greater detail.

In this figure, the cartridge 126 is shown to include an irrigation conduit 150 and an evacuation conduit 152, both of which lead to a central access conduit 154 which extends down the center of the male connector 134. Irrigation and evacuation procedures are controlled by irrigation and evacuation valves 156 and 158, respectively.

The irrigation valve 156 consists of a valve seal 160 mounted onto a stem which is screwed into an activator button 132a. A fluid tight seal is provided for the valve 156 by an O-ring 168 mounted onto the cap 132a. The valve seal 160 seals against a valve seat, formed at the junction between the irrigation conduit 150 and the central access conduit 154 and is held in the sealing position (as shown) by a spring 162.

Access to the valve seat is through a hole 164 formed into the top (as shown in the drawing) of the cartridge 126. This hole 164 can be closed off with a cap 166 and allows the irrigation valve 156 to be inserted into the cartridge 126. This is done by inserting the valve seal 160 and its associated stem into the hole 164 from above and inserting the spring 162 from below. Thereafter the cap 132a can be screwed onto the stem to hold the entire valve 156 in place.

To operate an irrigation procedure the button 132a is depressed to move the valve seal 160 clear of its seal to open a fluid path between the irrigation conduit and the central access conduit. Releasing the button 132a causes the spring 162 to force the seal 160 back into its seat thereby automatically shutting the valve.

The evacuation valve 158 is of a different construction. In this valve 158, the valve seal 170, in its off position as shown, seals the mouth of the evacuation conduit 152.

In operation, the seal 170 is moved under action of a plunger and evacuation button 132b from the position shown to a position 170' in which an end of a conduit 174, formed through the seal 170, aligns with the central access conduit 154. At the same time the other end of the conduit 174 is aligned with the evacuation conduit 152 and evacuation can be accomplished. By releasing the button 132b, the spring 172 biases the seal 170 back into its sealing position.

Assembly of this evacuation valve 158 is by inserting the entire valve mechanism into its valve bore and sealing a collar 176 in the bore.

As has been indicated with reference to FIG. 14, the cartridge 126 is of the disposable type and is intended for use only once. Accordingly the considerations of valve flushing (during cleaning) are not entirely applicable here.

In FIG. 16 yet another type of valve, which can be used as either an irrigation or an evacuation valve, is illustrated.

The valve, generally indicated as 180, is shown to include a hollow cylindrical valve body 182 which is sealed at its lower end by a valve seal 184 and at the other by an activator button 186. The activator button 186 seals against the valve body with an O-ring 188 and is connected to the valve seal 184 by means of a plunger 190.

To open the valve 180, the button 186 is depressed against the bias of a spring 192 to move the valve seal 184 to the position indicated in broken lines. This opens a fluid path 194 between an opening 196 formed in the sidewall of the valve body and its lower end. Releasing the button 186 allows the spring 192 to force the seal 184 back into the closed position.

One advantage of this valve is that it is very simple and inexpensive to manufacture and can, therefore, readily be disposed of.

Finally, it will be apparent to anyone skilled in the art, that the surgical instrument of this invention could be made from any suitable material. In the event that, the instrument is intended for single use, plastic material could be used. Alternatively, for reusable or reposable instrument, the instrument can be made of a more durable material.

FIG. 17 is a perspective view of an endoscopic surgical instrument 200 which is an alternate embodiment of the surgical instrument 20 described above. FIG. 18 is a partial sectional view of a portion of the instrument 200 taken along the line 18—18 of FIG. 17 and FIG. 19 is another view of the instrument 200 taken as indicated by the line 19—19 of FIG. 17. FIG. 20 illustrates the retractable electrode assembly 202. When viewed together, FIGS. 17–20, illustrate the instrument 200 including an endoscopic instrument 201, a retractable RF electrode assembly 202, an continuous irrigation and evacuation assembly 203, a R.F. energy source 285, and a tissue impedance monitoring device 284. It will be appreciated that, although two retractable RF electrodes are illustrated and subsequently described, in alternate embodiments the retractable electrode assembly could have one or more than two retractable RF electrodes. Also, although a bipolar retractable RF electrode assembly is illustrated and subsequently described, it will be appreciated that a monopolar retractable RF electrode assembly could be used.

The assembly 203 includes a housing 210, an irrigation valve assembly 214, and an evacuation valve assembly 220. The housing 210 includes an elongated portion 228 having a generally oval cross section. The portion 228 includes a free tip end 230 and a secured end which is attached to a handle portion 232. The portion 232 is held by the surgeon, and the portion 228 is surgically introduced into a body cavity (not shown) of the patient. A single access conduit 212 (a portion of which is best seen in FIGS. 18 and 19) is formed between an inner surface of the portion 228 and the objects carried within the portion 228. The conduit 212 is disposed along the entire longitudinal length of the portion 228 and is functionally similar to the conduit 25 (FIG. 2) in that it permits the irrigation and evacuation of fluids into and out from the body cavity into which the portion 228 is inserted. The conduit 212 is open at the tip end 230 and can be accessed, at its opposite end, via an aperture and associated closure 226 formed in the handle portion 232. The closure 226 is in the form of a tricuspid valve and is substantially similar to the valve 31 illustrated and described above (FIG. 2).

The irrigation valve and the evacuation valve assemblies 214, 220 are substantially similar to the irrigation and evacuation valves 23, 24 described above (FIG. 2). The valve assemblies 214, 220 operate in a similar manner to valves 23, 24 (FIGS. 7, 8). Depressing the valve assemblies 214 or 220 permits the communication of fluid in a valve first conduit 216 (or 222) with a valve second conduit 218 (or 224). Each of the valve second conduits 218 and 224 are in fluid communication with the conduit 212 (in the same manner that the conduits 23a, 24a are in fluid communication with the conduit 25, FIG. 2). Thus, when the valve assembly 214 is operated, irrigation fluid can be communicated to the conduit 212 and out through the tip end 230, and delivered to the body cavity. In a similar manner, fluids in the body cavity can be evacuated if the valve assembly 220 is operated.

The retractable electrode assembly 202 includes a means for guiding the angular orientation of the electrode or guide sheath 248, an endoscope sheath 238, a electrode movement mechanism 236, a tissue impedance measurement device 284, and a R.F. energy source 285. The sheath 248 is generally parallel to the scope sheath 238. The sheath 248 and the sheath 238 are each insertable into an opening of an insert flange 242, into the aperture of the handle portion 232 of the assembly 203. The sheath 248 and the sheath 238 are insertable within the conduit 212 and are each of sufficient length such that when each is fully inserted within the conduit 212, each extends slightly beyond the tip end 230 of the cylindrical portion 228.

The endoscopic instrument or endoscope 201 is substantially similar to the endoscope instrument described above, and can be any of a number of devices known in the prior art. An eyepiece 204 is shown attached to the endoscope 201. The endoscope 201 is slid into the scope sheath 238 until the eyepiece 204 engages a flange 240 which is attached to the sheath 238. Thus, the endoscope 201, and the sheath 248 of the retractable electrode assembly 202 are both insertable within the portion 228 of the irrigation and evacuation assembly 203.

Each of two RF electrodes 250a, 250b is sheathed within its respective guide sheath 248a, 248b. Although the illustrated embodiment depicts two RF electrodes, it will be appreciated that the assembly 202 could have one or more than two electrodes. Each electrode 250a, 250b includes a first or distal end 249a, 249b, a second, or proximal end 247a, 247b, and a central portion (not shown) disposedly connected therebetween. A coating of insulation 246 is disposed onto the bare electrode 250. The insulation coating 246 may be in the form of a tube of material (such as teflon) heat shrunk around the bare electrode 250. Alternately, the insulating coat 246 may be powder deposited, using vacuum deposition techniques, onto the bare electrode 250. In either case, nearly the entire length of the bare electrode 250 is covered by the insulating coat 246.

The electrodes 250a, 250b have a generally constant diameter throughout its entire length and are sized such that they can be slid within the sheaths 248a, 248b. That is, there exists a sufficient clearance (e.g. 0.005 inch) between the outside diameter of each of the insulating coats 246a, 246b of the electrodes 250a, 250b and the inner diameter of the respective sheaths 248a, 248b. Each electrode 250a, 250b is made from a superelastic metal material, e.g. typically a Nickel-Titanium (NiTi) metal alloy. The guide sheaths 248a, 248b are made from a rigid plastic or coated metal tubing which forms a rigid conduit that guides, i.e. deforms, the electrode along a predetermined path.

As best seen in FIG. 19, the electrodes 250a, 250b and their respective sheaths 248a, 248b are contained within the cross sectional envelope of the portion 228. Thus, the required incision into the patient need only accommodate the cross sectional area of the portion 228. The presence of the extendable electrodes does not increase the size of the required incision. It should be also noted that each electrode 250a, 250b descends downwardly into the field of view of the endoscope 201. In this manner the surgeon is able to view the extension of each electrode 250a, 250b beyond the end of the sheath 248a, 248b.

The two electrodes 250a, 250b and their respective insulators 246a, 246b are encased within their respective guide sheaths 248a, 248b which are encased within a plastic insulating covering 244. The electrodes 250a and 250b encased within the plastic covering 244 exits the housing 232 through the opening in the flange 242.

Each electrode 250a, 250b is in parallel electrical communication with a tissue impedance measuring device 284 and a R.F. energy source 285. The covering 244 enters the movement mechanism 236 through an opening 260 formed in a sleeve 256 of the mechanism 236. The electrodes 250a, 250b and their respective insulators 246a, 246b exit from the covering 244 and each of the second ends 247a, 247b, of each of the electrodes 250a, 250b are attached to connecting pins 272a, 272b, respectively. The connecting pins 272a, 272b are mounted at an end of a plunger 264. Each connecting pin 272a, 272b is in communication with a wire 274a, 274b each of which passes through the plunger 264, through an opening 278, and into an insulated line 276 which is terminated in a plug 280 which is matingly engagable with a receptacle 282 of the tissue impedance measuring device 284. The R.F. source 285 is in electrical communication with the impedance measuring device via electrical lines 283a and 283b. The source 285 and the impedance measuring device 284 are connectable in parallel in order to get realtime impedance measurement of tissue engaged between the first ends 249a, 249b of each of the electrode 250a, 250b.

The movement mechanism 236 includes a finger ring portion 252, and a thumb ring portion 254. The finger ring portion 252 is a generally flat plate having finger loops 251a, 251b formed therein. A passage 262 is formed through the finger ring portion 252 such that the longitudinal axis of the passage 262 is disposed between each finger loop and lies coplanar with the plane of each finger loop. The sleeve 256, and a cylinder 258 are partially inserted into opposite ends of the passage 262. The sleeve 256 has a passage longitudinally formed therein so as to receive the covering 244. The cylinder 258 has a passage longitudinally formed therein which is aligned with the passage of the sleeve. The plunger 264 is slidable within the passage of the cylinder 258. One end of the plunger is attached to the thumb ring portion 254, and the connection pins 272a, 272b are mounted to the other end of the plunger 264. The outer surface of the plunger 264 is visible through an access cutout 270 formed in the cylinder 258. In one embodiment, an indicator post 266 is attached to the outer surface of the plunger 264 and passes through the access cutout 270 to give an immediate visual indication of the position of the plunger 264 within the cylinder 258. In a preferred embodiment, the outer surface of the plunger 264 is scored with a plurality of indicator marks 268 to provide a visual indication of the position of the plunger 264 within the cylinder 258, which corresponds to variable length of extension of each of the electrodes beyond their respective insulating sheaths.

In operation, the irrigation and evacuation valves, and the endoscope operate as described above. Regarding the retractable electrode assembly 202, a free hand of the surgeon is used to operate the movement mechanism 236. The surgeon's fingers are engaged within the finger ring loops and the thumb is engaged within the thumb ring portion. The thumb either pushes or pulls on the thumb ring thereby moving the attached plunger 264 into or out of the cylinder 258 and the passage 262. As the plunger 264 moves each of the first ends 249a, 249b of each of the electrodes 250a, 250b move because the connection pins 272a, 272b mounted to the plunger are attached to each of the second ends 247a, 247b of each of the electrodes 250a, 250b. Thus, as the plunger moves in the direction of the arrow A, the central portions of each of the electrodes moves within their respective insulators in the direction of the arrow B, and the first ends 249a, 249b move in the direction of the arrow C.

FIG. 21 illustrates the first end 249 of the electrode 250. The guide sheath 248 is formed with a bend at one end. The electrode 250 slides within the sheath 248 and exits the sheath 248 under the guidance of the sheath 248. The insulating cover 246 permits the easy'sliding of the electrode within the sheath 248. Although a bend of 90 degrees is illustrated, it will be appreciated that a bend of any angle may be formed in the sheath 248 so as to guide the electrode 250 into a variety of angular dispositions. It should be noted that the electrode 250 is bare in the vicinity of the first end 249. A predetermined length value L, measured from the tip of the electrode to the end 255 of the insulating coat 246, represents the length of the electrode 250 that is bare or uncoated. Typical values for L range from 0 to 3 cm.

The first ends of each electrode extends beyond its respective sheath 248 by a length greater than the predetermined extension length L in order to permit the bare electrode to penetrate a tissue portion up to the full L value. Further, the first ends of each needle electrode are separated by a predetermined separation width W (typically 0.1–2.0 cm) and each first end forms a predetermined angle θ with respect to the longitudinal axis of portion 228. In the illustrated embodiment, the angle θ is 90 degrees. Typical values for θ range between 0 and 360 degrees.

During surgical procedures, the tip end 230 of the portion 228 of the instrument 200 is brought adjacent to a target tissue area of the body cavity. The first ends of each electrode are extended beyond their respective sheaths such that each first end is embedded into the soft target tissue area thereby defining a tissue portion engaged between the adjacent first ends of each electrode. The power source is energized and R.F. energy is transmitted from one electrode to the adjacent electrode. The energy transmission causes a coagulation of the tissue portion engaged between the adjacent electrodes and ablation of the target tissue.

Using the present invention, the surgeon can predict and control the amount of tissue ablation/coagulation with greater accuracy and safety. As described above, the spacing between the two parallel first ends of each electrode remains constant at some predetermined W value, e.g. 1.0 cm. Also, the extension of the electrodes beyond the insulators at a given angle, i.e. the depth. of penetration of each first ends of each electrode into the soft tissue portion, can be precisely controlled by observing the indicator marks on the plunger. Predictable and precise tissue ablation is therefore possible with the present invention because the depth of each first end of each electrode in soft tissue can be precisely controlled by the surgeon. That is, the surgeon can predict a cylindrical zone of ablation by controlling the depth of the retractable first ends into the soft tissue portion. This precise depth control enables the surgeon to predict the zone of ablation with greater accuracy and safety than prior art non-retractable monopolar RF devices, or prior art laser delivery systems.

The cellular structure of body tissue contains water which is a conductor of electrical energy. Consequently, a portion of body tissue also has an associated resistance or impedance value. In prior art monopolar electrode devices, tissue impedance is difficult to measure. However, in the present invention, precise impedance measurement of the soft tissue in the proximity of the bipolar electrodes is possible. In the present invention, during the tissue coagulation process simultaneous measurement of the impedance of the tissue engaged between the extended first ends of the electrodes signals the completion of the tissue coagulation process and provides assurance and confirmation to the surgeon.

R.F. energy applied to the tissue engaged between the first ends of the two electrodes causes the tissue to coagulate which decreases the water content associated with the tissue. As the water content decreases the conductivity of the tissue decreases. For a constant R.F. energy, as the conductivity decreases the impedance (or resistance) associated with the tissue increases. The tissue impedance is highest when the tissue is completely coagulated, since coagulated tissue has a minimum amount of water content and current flow is blocked from one electrode to the other electrode. However, at the beginning of the ablation procedure, the tissue impedance is at a minimum because the water content of the tissue is at its highest level and the tissue is a good conductor and allows the maximum current to flow from one electrode to the other. During the ablation procedure, as the tissue coagulates the water content decreases and the tissue impedance increases. The tissue impedance measurement device 284 can be designed to transmit an variable frequency audible signal, i.e. a beeping tone, when the tissue impedance is at its lowest value. As more tissue is ablated and as the tissue impedance reaches its highest value the audible signal decreases in frequency. In the present invention, the tissue impedance is monitored or measured on a relative basis. That is, the impedance measured or monitored is the impedance of the tissue engaged between the two needle electrodes.

FIGS. 22A through 22H illustrate alternate electrode configurations. It will be noted that the preferred embodiment of the present invention includes two electrodes with a θ of 90 degrees, and a L value of 0–3 cm, and a W value of 0.1–2.0 cm. It will be appreciated that a variety of electrode configurations, with associated L, W, and θ values within the above specified ranges, are possible. However, it is generally preferable to limit the total number of electrodes to six or less.

It will be noted that in the embodiments illustrated in FIGS. 22A–22C, 22G–22H, the electrodes 250 are guided by the shape of the sheath 248. That is, the electrodes can be directed towards or away from each other if the guide sheaths are angled towards or away from each other. Similarly, different θ values are possible if the sheaths are formed with the appropriately angled bends.

Figure 23:
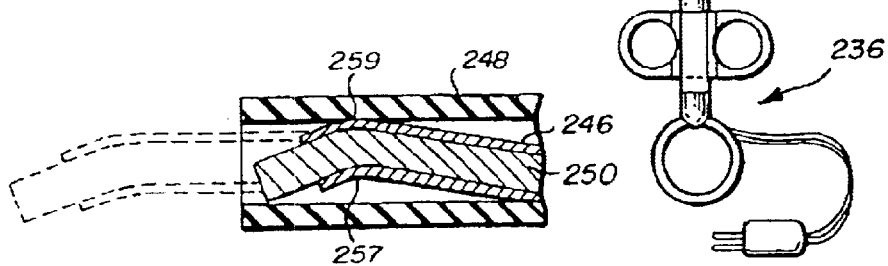
FIG. 23 is an enlarged view of the tip of the retractable electrode shown in FIGS. 22D–22F.

However, in the embodiments illustrated in FIGS. 22D–22F, the sheaths are substantially straight and the electrodes themselves are bent in order to direct them in certain orientations. This feature is more clearly shown in FIG. 23 which illustrates a typical electrode having a bend formed at the location depicted by numeral 257. When the electrode is disposed within the sheath 248, the electrode 250 is in contact with at least one portion 259 of the inner surface of the sheath 248 because of the bend 257. When the electrode is extended beyond the sheath (shown in phantom lines), the electrode "flattens" within the sheath 248 while the electrode tip angles away from the sheath centerline in accordance with the bend 257 formed in the electrode.

Figure 24:
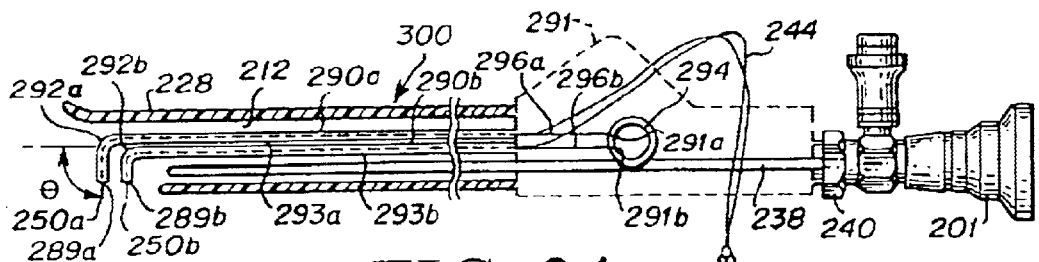
FIG. 24 is an alternate embodiment of the present invention including a retractable electrode assembly having a variable angle control mechanism.

FIG. 24 illustrates a retractable electrode surgical instrument 300 which is an alternate embodiment of the retractable electrode instrument 200 (FIG. 17). The instrument 300 includes many of the same elements as the instrument 200. These identical elements are identified with the same reference numeral as shown in FIG. 17. In this embodiment, each electrode 250a, 250b is enclosed within a bendable guiding sheath 290a, 290b. A guide wire 293a, 293b is disposed within each sheath 290a, 290b and includes a first end 289a, 289b and a second end 291a, 291b. Each first end 289 of each guide wire 293 is attached (e.g. welded or adhesively bonded) to an inner surface of a bendable or bellows portion 292 of the sheath 290 at a location proximate the open end of the sheath 290. Each second end 291 is attached to a lever or knob 294 which is mounted to an outer surface of a housing 291. The housing 291 is similar to the housing 232 and includes communication ports for an irrigation valve and an evacuation valve (neither shown). In operation, when there is no tension on the guide wires the sheaths are straight within the conduit, i.e. θ is 0 degrees. As the surgeon pulls back on the knob or lever, the wires are tensioned and the tips of each sheath is pulled back as illustrated until a desired θ value is obtained. In this embodiment, both the L and the θ values can be adjusted by the surgeon in situ.

With reference to FIG. 25, alternative embodiments for the electrodes of the present invention are shown. FIG. 25(a) illustrates an electrode configuration similar to that shown in FIG. 22(a) except that two pairs of bipolar electrodes 350a and 350b are used. FIG. 25(a) shows the electrodes 350(a) and 350(b) extending outward from sheaths 348(a) and 348(b) at the distal end 349. Electrodes 350(a) are preferably either both active or both passive, while the pair of electrodes 350b encased in sheaths 348b have the opposite polarity. Alternatively, the electrodes can have crosspolarity. The configuration shown in FIG. 25(a) creates an approximately square or rectangular pattern of electrodes (depending upon spacing of 350a and 350b). The sheaths and electrodes are shown bent at an angle of approximately 90 degrees, but other angles are useful as well, and are included in the spirit of the invention. Although four sheath and electrode pairs are described with two as preferably receiving the active voltage/power and the other two as ground, or i.e. passive, various other combinations are possible and included in the invention. A few of these possibilities are illustrated through use of FIGS. 25(b)–25(f) which show views of the ends of the sheaths and electrodes, omitting other details-for clarity. For example, FIG. 25(b) illustrates the arrangement of electrodes in FIG. 25(a). With electrodes 350(a) active and 350(b) passive, electric fields will extend between the two pairs approximately as shown by the dotted lines. The tissue will be heated in a volume having a cross section which can be seen to be an approximate square or rectangular, depending on the spacing of the electrodes. The pattern for two electrodes (i.e. a bipolar electrode) is shown in FIG. 25(c). The volume of tissue ablation is controlled by the depth of insertion of the needle electrodes into the tissue.

Another alternative is shown in FIG. 25(d) in which two passive electrodes 350a are used with a third active electrode 350b, resulting in a generally circular cross sectional area of tissue ablation. Use of more electrodes will provide a more circular cross-section. As examples, FIGS. 25(e) and 25(f) are further variations which result in circular tissue ablation, both utilizing an active electrode 350b surrounded by passive electrodes 350a. In all of the above described configurations, energy is passed from one electrode or electrodes to another electrode or electrodes, through tissue in between, causing it to be heated. The preferred number of passive electrodes for circular tissue coagulation is in the range from 3 up to a maximum of 16. For optimal distribution of energy from the electrodes, it is preferred that the sum of areas of the active electrodes (designated as 350b in FIG. 25) be approximately equal to the sum of the areas of the passive electrode(s) 350a.

FIG. 26 shows an embodiment of the present invention providing a circular zone of coagulation of adjustable diameter. Active electrode 350b is surrounded in a circular pattern by passive electrodes 352. Electrodes 352 are superelastic metal "memory wires" such as nickel-titanium wires which are pretensioned to a bowed shape or angle. While the electrodes are inside of tubes 354, they are held in straight position. When the electrodes are advanced outside of tubes 354, they angle outward from the central axis of the supporting tube 354. Electrode 350b is straight and preferably carries the active energy from the RF power source. In operation, the electrodes 352 and 350b are all connected to the electrode moving mechanism 236 (FIG. 20) and moved in and out together. Alternately, electrode 350b may be independently moved relative to the other electrodes 352, thus allowing for significant flexibility in adjusting the area of ablation or coagulation. For clarity of illustration, only a portion of the tubes and electrodes is shown. The assembly is shown cut off at 355, but actually extends in length, the electrodes 352 and 350b having a proximal end (not shown) which connects to the electrode moving mechanism, which in turn connects the electrodes to an RF energy source, for transmitting the power to the distal ends at 353. The dashed lines in FIG. 26(a) illustrate the movement of electrodes 350b and 352, the central electrode 350b being coaxial with the central axis and preferably extending or retracting independently of electrodes 352. As shown by the dashed lines, electrodes 352 may be extended outward and away from electrode 350b, the greater extension providing a greater cross-section of ablation/coagulation. The end of central electrode 350b is extended into the same plane as the ends of electrodes 352 for coagulation of a volume of tissue having a circular cross sectional area.

Use of superelastic "memory wires" which exit the tubes 354 at predetermined angles is preferred. Another method of angling the electrodes outward is more clearly shown in FIG. 26(b) illustrating one of the tubes 354 with an electrode 352 installed therein. The pre-induced angle of electrode 352 causes it to bear against the interior wall 356 and the rim 358 of the opening 360. The structure of tube 354 and electrode 352 combination (as shown in the figure) requires tube 354 to be constructed of an electrically insulating material since no coating is shown on electrode 352. Alternatively, or in addition to having tube 354 non-conductive, the electrode wires can be insulated with a thin non-conductive coating except for the end portion of the wires. In this manner, the only active portions of the electrodes are those portions which do not have the non-conductive coating.

FIG. 26(a) shows a grouping of six tubes enclosing electrodes 352, and one tube with an electrode 350b. Although six tubes 354 are shown, the invention also includes other numbers of tubes, electrodes, and configurations, including such configurations corresponding to the patterns illustrated in FIGS. 25(b) to 25(f). Arrangement of electrodes in a different pattern can be done to obtain coagulation of a volume of tissue having a rectangular, circular or other cross section. As an alternate construction, the tubes 354 and 362 could be merged in one continuous piece of material with the required bores for guiding the electrodes formed therethrough. Such an embodiment would look similar to the cylindrical section of the embodiment to be described in FIG. 27. Note that the further the electrodes are advanced out of the tubes into body tissue, the greater will be the volume of tissue coagulated, as the tissue provides a conductive path for the RF energy along the lengths of the electrodes inserted in the tissue.

Referring now to FIG. 27, there is shown an alternate embodiment for accomplishing a similar purpose as presented in regard to the embodiment of FIG. 26. Instead of angular memory wire electrodes, all of electrodes 366 are straight, and preferably constructed of superelastic conductive material, such as nickel titanium wire. Electrodes 366 as well as central electrode 368 are all guided by holes 370 through the first section 372 of the guiding structure 373. The structure 373 has a conical shaped end section 374, the narrow end of which is connected to a first end face 376 from which electrodes 366 emerge, and extends from the face 376 to a wide end 378 from which the central electrode 368 emerges. The conical shape 374 interferes with the electrodes 366, deflecting them outward from the central axis 375 away from the central electrode 368. This provides a method for varying the angle of deflection from the central axis, and thereby achieving a larger or smaller cross section of tissue coagulation, with end sections using different angles for the conical shape.

As with the embodiment of FIG. 26, the further the electrodes 366 are protruded from the casing 372, the farther they extend from the central electrode 368, creating a larger area of ablation/coagulation. The electrodes' proximal ends at 380 are to be connected to an electrode movement mechanism such as 236 shown in FIG. 20.

FIG. 28 illustrates a connecting cable assembly 394 for an RF generator system utilizing the apparatus above described, and additionally has the facility for providing either monopolar RF power to the electrodes for tissue cutting/coagulation or bipolar power for coagulation procedures. The use of the monopolar RF power between two electrodes in close proximity has not been addressed in the prior art, and will be shown to have significant advantages. In the prior art, monopolar electrodes have been used with a patient return pad to complete the electrical path. Monopolar applications use higher RF power, typically for tissue cutting and coagulation. The use of patient return pads creates an electrical path from the active monopolar electrode to the return, pad. This path therefore tends to be relatively long, unpredictable, and unsafe.

The single connecting cable system shown in FIG. 28 allows the surgeon to use one instrument either in monopolar or bipolar mode. The single cable system also eliminates the need for patient return grounding pads and the associated risk of "stray currents" and adjacent tissue damage. In FIG. 28, cable assembly 394 includes two bipolar cables 396 and 398 having banana plugs 400 and 402, each of the cables 396 and 398 leading from an interconnection block 404. The banana plugs 400 and 402 are for interconnection with bipolar receptacles 406 and 408 of RF generator 410. There is a monopolar output cable 412 leading from the interconnection block 404 with a monopolar plug 414 for interconnection with monopolar receptacle 416 of the RF generator 410 (receptacle 416 is typically labelled "Foot Control" in commercially available RF generators). A return path cable 418 is shown leading from the interconnection block 404, and has a connector 420 for mating with receptacle 422 of the RF generator 410 (receptacle 422 is typically labelled "Patient Return"). The function of the interconnection block is to join the bipolar cables 396 and 398 to the monopolar output cable 412 and return path cable 418. The block 404 then connects the resultant two wires to an output cable 424 which passes the RF power through a connector assembly 425 to electrode movement mechanism 236 which in turn connects the power to the electrodes.

The RF generator 410 is a standard energy source in the industry, and has facility for switching the power output either to the higher power level for use in the monopolar mode for cut/coagulation, or to the lower power bipolar mode for coagulation. FIG. 28 also shows a standard foot pedal 426 interconnected with the RF power generator 410 through cable 428 for turning the RF power output of the generator 410 off or on in cut or coagulation mode.

The above described cable assembly is used with the above described endoscopic surgical instrument to allow either monopolar or bipolar power to be supplied to the electrodes without having to manually connect and disconnect separate cables to RF generator 410.

The convenience of being able to select either monopolar or a bipolar energy for application to a single electrode assembly gives a surgeon significantly enhanced surgical capability and convenience in the monopolar mode, ablation and removal of tissue is possible, and in the bipolar mode, coagulation is possible, allowing the surgeon to make decisions after insertion of a single electrode apparatus. Previously, use of electrodes in bipolar and monopolar modes required time consuming removal of electrodes and complete change of operating procedures and instrumentation.

Method for Removing Uterine Fibroids

Over thirty percent of women between 30 and 50 years of age have uterine fibroids, which can cause abnormal bleeding and associated problems. There are three major kinds of fibroids:

(1) subserosal fibroids which are located outside the wall of the uterus; (2) intramural fibroids which are located inside the uterine wall; and (3) submucosal fibroids which are located outside the endometrium. The majority of fibroids needing treatment to prevent abnormal bleeding are the submucosal type. Treatment options for uterine fibroids have included drug therapy and surgical treatment. Drug therapy is used to shrink the fibroid, but is expensive and fibroids return to their original size within four months of ceasing use of the drug therapy. Surgical treatment such as myomectomy or hysterectomy involve significant hospital stay and recovery time as well as high costs. Alternative treatments therefore are preferred to drug therapy or surgical treatment.

Laparoscopic myoma coagulation is used for the treatment of subserosal and intramural fibroids. Submucosal fibroids cannot be treated laparoscopically due to the need for an internal incision and closure of the uterine wall. Laparoscopic coagulation uses a Nd:YAG laser or bipolar/monopolar electrosurgical electrodes to shrink the fibroids.

The prior art use of R.F. needle electrodes for laparoscopic coagulation has been limited to a single monopolar electrode or to a pair of bipolar electrodes for laparoscopic treatment of uterine fibroids because the prior art electrodes can only be used along the axis of visualization of the laparoscope. Additionally, the prior art single monopolar or pair of bipolar electrodes have provided only a limited area of tissue coagulation. The electrodes of the present invention as described above, provide a larger zone of coagulation, and may be used for laparoscopic or hysteroscopic treatment of uterine fibroids. The needle electrodes described herein may be introduced to the sidewall of the uterus at any angle to the axis of visualization of the hysteroscope.

The flexible needle electrodes of the present invention allow the angle of entry to tissue (relative to the axis of the probe) to be adjusted to any angle. Moreover, the use of multiple electrodes with an adjustable angle of entry to tissue, allows a larger sized area of tissue coagulation, including areas which have greater area than the size of the probe which guides the needle electrodes to the tissue insertion site.

The present invention treats uterine fibroids with hysteroscopic myolysis. The uterine fibroids are first identified using hysteroscopy, endovaginal ultrasound, computerized axial tomography, or MRI to allow visualization of the interior of the uterine cavity. By such imaging of the uterine cavity, the size, shape and position of any fibroid can be determined. Hysteroscopic myolysis can then be performed using a monopolar needle electrode, or one of the bipolar needle electrode configurations of the present invention as above described. To protect the rectum, bladder and blood vessels of the uterus, vaginal ultrasound is used to determine the fibroid's posterior surface prior to insertion of the electrode(s). The R.F. needle electrodes are then inserted through an operating hysteroscope. The electrodes can then be manipulated and inserted in the fibroids to the desired depth under direct visualization of the hysteroscope, and the area surrounding the electrodes may be coagulated. By repeatedly puncturing the fibroid with the needle electrodes, the entire fibroid can be coagulated.

This disclosure addresses uterine fibroid treatment in particular. However, the method described can be used for ablation/removal of any soft tissue, such as breast; liver, colon, and prostate tumors/growths. FIG. 33 shows an alternative endoscopic surgical instrument 431. An RF electrode 432 with a field enhancement tip 476 is installed in an alternative style of retractable RF electrode assembly 430. The electrode 432 can also be used with the assembly 203 of FIG. 17 or any other compatible assembly structure. The apparatus of FIG. 33 includes an outer housing 434 that has a large outer sheath 436 extending from the connection end 438 to the distal end 440, the outer sheath enlargened slightly at 442 over the length of a perforated end section 444. The housing 434 has a handle grip 446 and a suction port 448, the port 448 terminating in a valve 450 followed by a Luer connector 452 for connection to a suction line (not shown). The housing 434 has a housing connector receptacle 454 for engagement with a mating sleeve 456, the substantial portion of which is inside receptacle 454 and not visible as illustrated. The mating sleeve 456 is part of a conduit housing and electrode movement assembly 457. An inner sheath 460 is shown inserted through the outer sheath 436 and terminating at end 462. The mating sleeve 456 and receptacle 454 secure the assembly 457 to the housing 434. The block 458 in combination with guides 464 and 466, RF connector block 468, spring 470, thumb ring 472, and end plate 474 provide for movement of the RF electrode 432 position. In particular, the distance of the tip 476 can be adjusted relative to the end 462. The block 458 also has irrigation port 478 attached, having a valve 480 and Luer fitting 482 for connection to an irrigation fluid supply line (not shown).

The inner sheath 460 is a cylindrical tubing with two annular openings therethrough including a first opening 484 extending through the sheath 460 and from end 486 through the plate 474, guide 464, and through the housing 458. The opening 484 is for insertion of the endoscope 489 probe 488 extending from the telescope 490. The plate 474 has a connector receptacle 492 which receives an endoscope mating portion 494, and locks the telescope in place with the assembly 457.

Irrigation fluid going through port 478 passes into a passage in block 458 and into bore 484 to pass through clearance between the bore 484 and the endoscope probe 488 to exit out the end 462 of sheath 460. Debris to be evacuated is pulled through holes 492 and passes along clearance 494 between the sheath 460 and the bore 436 to exit via a hole in the bore 436 to pipe 448.

The electrode 432 has an elongated stem 496 that is inserted through the second annular opening 498, through the inner sheath 460 and block 458 to exit at face 500. The stem then enters connector block 468 where an RF connection end of the electrode stem is connected by a spring loaded latch mechanism 504 and placed in electrical contact with the center pin of RF connector plug 502. The assembly 430 as shown in FIG. 33 is one of a number of existing assemblies that are used for inserting an endoscope and an RF probe into a patient, including assemblies with electrode movement mechanisms such as 236 in FIG. 17. The present invention includes RF electrode 432 having a novel field enhancement tip 476, the various embodiments of which will be fully explained in reference to the following figures of the drawing.

FIG. 33 also illustrates the use of the apparatus in either monopolar or bipolar operation. For the purpose of this discussion, monopolar mode is defined as that mode of operation using an external body pad such as 802 in the electrical return path to the RF generator. Bipolar operation is when the return path is through a conductive element located relatively near the electrode tip that is connected to the RF generator active side. Generally, such a conductive element for bipolar operation will be within the patient's body. For the following disclosure, the electrode tip 476 of FIG. 33 and the conductive element used to receive RF energy for the return path can be of any electrode type, including one or more needle tips, rollers, loops, disks, etc. Examples of needle tips are those of FIGS. 17–27, and loops and rollers are exemplified in FIGS. 44–61. The preferred embodiment for bipolar operation utilizes the endoscope probe outer sheath 436 as the return electrode. In this case, the sheath is constructed of an electrically conductive material, and connection to the RF generator is made by any of various ways known to those skilled in the art. The preferred method of connection will be described in the following detailed description. Alternatively, any portion of the sheath, or any conductive element can be positioned at or near the distal tip end of the probe to function as a return electrode, and electrical connection can be made by a conductor alongside or interior to the probe. For example; the perforated section 444 could be constructed of electrically conductive material to serve as a conductive element for the return path, with the remainder of the housing 434 constructed of insulative material. In such a case, a separate conductive line would have to be used to connect the section 444 to a connector for attachment to a line from the RF generator passive side 810.

FIG. 33 also illustrates the use of a fluid 828, which can be either isotonic or non-isotonic, for use in either monopolar or bipolar mode, the use depending on the system requirements which will be discussed in the following description. Operating the apparatus of FIG. 33 involves bringing the electrode tip 476 into contact with a tissue surface 800. In the case of monopolar operation, a conductive return pad 802 is placed on a body exterior 804 area in closest proximity to the tip 476, and is connected electrically as indicated by line 806 to the return/passive side 810 of an RF generator 812. The line 806 is shown partially in dashed lines 808 to indicate that it is an alternative to a connection for bipolar operation.

The preferred bipolar connection, applicable for example when the endoscope probe outer sheath 436 is used as the return electrode, is indicated by line 814 to the conductive housing 458 and outer sheath 436 by way of the Luer fitting 452, valve 450 and line 448, all constructed of electrically conductive material. Various ways of making electrical contact to the sheath 436 will be apparent to those skilled in the art, and these are indicated in the spirit of the present invention. The preferred method of making electrical contact from the passive side of the RF generator to the Luer fitting 452 is through use of an adapter 816. The adapter 816 provides passage of fluid from Luer connector 452 to a Luer type connector 817. A lever 819 is shown, indicating the option/alternative of having a fluid valve in the adapter 816. The adapter 816 has a banana plug 821 attached for connection to a receptacle 823 providing connection to line 814 to the passive side 810 of the RF generator 812.

The active side 820 of the RF generator is preferably connected to the probe 476 as follows. The electrical line 818 carries the RF energy from the supply 812 active terminal 820 of RF generator 812 to connector 502, from which the RF energy is carried to the tip 476 by way of a conductive center conductor in the insulated electrode stem 496, which will be shown in detail in FIGS. 34A–34C. The mating connector 503, connecting line 818 to connector 502 is shown in dashed lines so as not to confuse it as part of a spring loaded locking device. 504 which extends to a groove in the electrode connective end to captivate the electrode in place. Such grooves are noted as 835 in FIG. 35B and 861 and 863 in FIG. 34D. The details of such a captivation device and equivalents will be understood by those skilled in the art.

An electrode embodiment using two electrode tips for bipolar operation is shown in FIG. 34D. In this case, one of the tips, for example 848, connected to connector 862 receives energy from the active side of the RF generator through line 818 and connector apparatus 502 and 504 as described above. The other electrode 854, connected to connector 864 is preferably connected to the passive side 810 of the RF generator by way of a second line and connection system similar to line 818 and connection apparatus 502 and 504. This is indicated symbolically in FIG. 33 by dashed line 819. The details of the dual electrode of FIG. 34D will be fully described in the following text in reference to the figure.

In monopolar mode, the RF energy is conducted by the tissue 822 between the tip 476 and the return pad 802 as indicated by the dashed lines 824. Although the greatest tissue heating occurs near the tip 476 as indicated by the closer spacing of the lines 824, all of the tissue between the tip 476 and pad 802 is heated to some degree. This is a disadvantage of the monopolar mode when the tissue requiring treatment is localized to a relatively small surface area, because healthy tissue can be damaged by stray RF current to some degree. In monopolar operation, a fluid 828 can be applied for improving contact between the electrode tip and the tissue surface 800. This fluid can be either isotonic or non-isotonic. Isotonic fluid is defined as electrically conductive fluid such as a 0.9% saline solution.

In those cases where the tissue area to be treated is localized near the surface 800, a bipolar connection of the apparatus is preferred because it confines the RF energy to a smaller area. As described above, the preferred arrangement for bipolar operation is accomplished by connection of the passive terminal 810 of the RF generator 812 to the metal housing 434 by way of line 814, connector 823, adapter 816 and valve 452 which makes electrical contact with housing 434. With this bipolar connection, the RF energy passes between the tip 476 and the housing 434, as indicated by dashed lines 826, the field concentrated near the perforated end section 444 of housing 434, i.e., the tip of the resectoscope.

Due to the uncertain electrical connection between the end section (tip of resectoscope) 444 and the tissue surface 800, a preferred method of operation in this bipolar arrangement uses a fluid 828 applied between the tissue and end section 444. This fluid can be either isotonic or non-isotonic, but the preferred embodiment uses an isotonic fluid, and the preferred isotonic fluid 828 is a 0.9% saline solution. The isotonic fluid 828 conducts RF energy from the tip 476 to the tissue 800 and from the tissue 800 to the sheath 436 of housing 434, and enhances the tissue heating by providing a more conductive electrical path from the tip 476 to the RF generator.

FIG. 34 shows an electrode 506 according to the present invention, with an elongated stem 507 allowing use with the device of FIG. 33 or similar commercially available device. Other forms of stem or i.e. connective line to electrode movement means of different design are also included in the present invention, such as an elongated flexible shaft for use with the device of FIG. 17. A novel feature according to the present invention is the incorporation of an RF field enhancement tip in the form of a roller 508 having narrow edged energy directors 510. The roller bar 508 is rotatably mounted on a straight, uninsulated portion 512 of the loop 509 joining conductive branches 513 and 514.

The electrode stem 507 has a conductive connecting end 516 with a notch 518 for connection by the means 504 referred to in the discussion of FIG. 33, for making contact with plug 502. Plug 502 in turn is connected to an RF power supply. In the various figures of the drawing, the electrode tips are all drawn showing a wire or wires leading from them. For brevity, the figures are drawn in simplified schematic form. In addition, two wires from a single tip are assumed to be connected together such as the branches 513, 514 in the tip of FIG. 34. In operation, the wires (branches) are connected to a stem and then to an RF power supply. In bipolar mode, two electrodes are used, and are shown in the figures with an independent wire leading from each of the electrodes. One of these wires is to be assumed connected, in operation, to one side (first side) of an RF power supply, and the other is to be assumed connected to the other side (second side) of the RF supply. Referring again to FIG. 34, a single conductor 520 extends from the connecting end 516 to junction 522 where the conductor joins the two branches 513 and. 514 which are joined by the straight uninsulated portion 512. The conductor 520 and branches 513 and 514 are covered with insulation 524. The straight portion 512 is not insulated in order to make contact with the roller 508. A metal guide sheath 526 covers the insulation 524 over a portion of the conductor 520 to provide guidance and rigidity to the electrode 506 as it is forced by the movement of block 468 to move in the second annular opening 498 of the inner sheath 460 of the resectoscope as shown in FIG. 33.

The electrode stem 507, as mentioned above, can be whatever configuration is required to conform to the particular electrode movement device used. FIGS. 34A, 34B and 34C show an alternative stem design 830 that includes a telescope guide 832 and insulation covering 834 over the conductor 836, both constructed of electrically insulative material. The proximal end 837 has a connector plug 839 for mating with a corresponding receptacle connected to a line for connecting to a terminal (preferably active side) of an RF signal generator. The design of FIGS. 34A–34C does not use a bare metal sheath over the insulation 834. If a metal sheath is required, such as for providing rigidity to the stem 496, it is preferably also covered with insulative material. The electrode configuration of FIGS. 34A–34C allows the electrode and a telescope to pass through a single bore in an endoscope probe housing, such as 434 in FIG. 33. This is illustrated more clearly in FIG. 34E, showing the housing 434 with the alternative stem design 830 and an endoscopic telescope 838 guided by the non-conductive saddle shaped telescope guide 832. The purpose of the insulative covering 834 and the telescope guide 832 constructed of electrically insulative material is to give assurance that all of the RF energy is transmitted at the electrode tip, and that no RF energy can pass/leak directly from the conductor 836 to the endoscope housing 434 in which it is positioned, thus minimizing RF energy loss. The saddle shaped telescope guide shown in FIGS. 34A–34C is given by way of example and as the preferred embodiment. Other telescope guide structures will be apparent to those skilled in the art and are included in the spirit of the present invention. For example, the guide could be a 360° C. circular loop of insulative material, etc.

The tip 840 of FIG. 34A is a wire loop for cutting tissue. The cross section and surface of the wire can be configured in any manner. For example, the cross section can be circular, rectangular, triangular or a flat ribbon. The surface finish of the wire can be serrated, knurled, slotted, etc.

The roller tip 842 of FIG. 34B can be used for coagulation, and the tip 844 of FIG. 34C demonstrates the use of protrusions, i.e. energy directors on the roller, having extremities of smaller area providing RF field enhancement with corresponding higher power density for vaporizing tissue.

FIG. 34D illustrates an electrode apparatus 846 having two tips for bipolar operation. A first electrode tip 848 makes electrical contact to a first conductor 850 of stem 852. A second tip 854 makes electrical contact with a second conductor 856 of stem 852. The stem has insulation 858 for electrically isolating the first and second conductors from each other, and from surrounding apparatus including the endoscope inner sheath 460, for example of FIG. 33, when installed. The proximal end 860 of the electrode apparatus 846 has connector elements 862 and 864 for making electrical contact to corresponding mating connectors to electrical lines leading in the active and passive sides of an RF generator. The details discussed above relating to the construction of electrode devices in FIGS. 34A–34E apply as well to electrode devices without the telescope guide, such as the electrode device shown in FIG. 33. The tips involving rollers and loops shown in FIGS. 34A–34E are also given by way of example, and other types of tips are also included in the spirit of the present invention. For example, a single or multiple needle probe could be used. The dual conductive support such as 850 and 856 and corresponding items in FIGS. 34A–34C are also given as examples, and other constructions which will be apparent to those skilled in the art are also included in the spirit of the present invention. For example, if a needle tip is used, only a single conductive line would be required to support it, rather than the two lines such as 850 used to support a roller or loop.

An alternate feature involving the electrode 506 is shown in FIG. 35 illustrating portion 525 of FIG. 34 showing an electrode tip to shaft connection 527 that when incorporated allows an RF electrode tip module 529 to be removed from a stem 531 and replaced. The electrode tip connector as illustrated in FIG. 35 includes a plug 533 having a tip 535 that is forced into slot 537 in the wall receptacle 539. The tolerancing of the bore 541 of the thin walled receptacle 539 relative to the diameter 543 and size of tip 535 of the latch 533 allows the receptacle wall, constructed of resilient materials, to yield to the entrance of the plug and retain the tip in the slot by resilient receptacle wall pressure. An alternate tip module 544 and mating stem 546 are shown in FIGS. 36 and 37. The tip module 544 has a straight plug 543 which engages in a leaf spring connector 550. The connector 550 is formed by boring a hole 552 in the conductor 520, forming slots 554 in the wall 556 to create leaf springs 558 which are compressed and usually heat treated. A spring latch 560 is mounted to the metal sleeve 526 and has a hooked end 562 for engagement in the y-space 564 of the tip module 544, as shown in FIG. 37 to retain the tip 544 in engagement with the stem 546. The arm 561 is a flexible resilient member allowing the latch 560 to be positioned as indicated by the dashed outline 563 so as to provide clearance for the plug 543 to engage in the connector 550, and to then allow the loaded end 562 to enter the y-space 564. Other means for connecting the tip module to the stem will be understood by those skilled in the art, and are also included in the present invention. The primary benefit of the tip module is the ability to mount any of a variety of tips, e.g. roller bar, cutting loop, vaporizing loop, etc. without having to also replace the stem. This results in a cost reduction, and offers greater variety during surgery. Any of the variety of tips described in this specification can be used with the tip module. The tip 548 shown in FIGS. 36 and 37 is a roller tip. FIGS. 38–40 illustrate the use of a roller (FIG. 38), cutting loop (FIG. 39) and dual rollers (FIG. 40). Although FIG. 40 as well as other figures of the drawing show only two electrode tips per electrode or tip module, the spirit of the present invention includes any number of electrode tips per electrode or tip module. For example, the rapid removal of larger areas of tissue may be facilitated by an electrode with a larger array of tips.

The tip modules can also be used in pairs for bipolar operation. For this purpose two modules can either be mounted/fabricated as an integrated unit and connected to a corresponding dual stem to transfer electrode movement and RF power to the tips, or each module can be separately attached to an independently controlled stem.

Referring now to FIG. 41, the roller 508 and conductor portion 512 are more clearly shown in the cross-section 31—31 of FIG. 34A. The roller 508 is shown to have a bore 564 therethrough for passage of the uninsulated conductor portion 512, which is bent at each end to form the conductor of branches 513 and 514 covered with insulation 524. The roller 508 has energy directors 566 with reduced area narrow edged surfaces 568 created by the formation of V shaped grooves 570 in the roller 508. The narrow surfaces 568 concentrate RF electromagnetic fields, increasing the RF power density so as to provide tissue vaporization. The benefit of the high energy density is that tissue can be vaporized in the localized, controlled area of the roller, and at the same time the resulting underlying tissue is subjected to enough heat to cause tissue coagulation. The significant field enhancement provided by an electrode tip with energy directors having reduced area extensions compared with a prior art electrode design is illustrated in FIGS. 42 and 43. The sharp edges 572 of the electrode 574 of FIG. 42 generates very high RF field concentration. The prior art device 576 of FIG. 43 by comparison generates lower power density. The RF energy is slightly concentrated only at the edges 578 of the roller.

The rolling action of roller 508 provides a benefit that is illustrated in FIG. 44, which shows the roller 508, part of branches 513, 514 and portion 512. The roller 508 is pressed against tissue 580, a first layer 582 of which is vaporized as indicated by arrows 584. The tissue layer 586, exposed due to vaporization of layer 582, is subjected to enough heat for coagulation. The rolling action of roller 508 indicated by arrows 588 helps to overcome the impediment of sticking tissue. As the roller is pulled in the direction of arrow 590 over the tissue 580, a fresh roller surface is continually presented at 592. The upward thrust of the roller at point 594 encourages the coagulated, sticking tissue 586 to pull away from the roller. The sticking of tissue to the roller is also controlled by the fact that since the heat is generated in the tissue, the roller portion 596 that is not in contact with the tissue has some time to "cool" before coming in contact with the tissue again at point 592. The rolling action therefore results in a greater rate of vaporization, and reduced tissue sticking.

The present invention also includes selected tip surface material to minimize sticking of tissue. The preferred embodiment is a gold surface, but other materials for reducing sticking are also included such as silver.

The roller 508, through operation of the electrode in back and forth movement using a device such as that of FIG. 33, can be passed repeatedly over a selected tissue area to vaporize successive layers of tissue that need to be removed. The use of the electrode as illustrated in FIG. 44 is in what is called a monopolar mode, where RF voltage is applied between the electrode roller and a return plate (not shown) which is normally attached to an exterior body surface in closest proximity to the roller 508.

The roller configuration of FIG. 44 is an example and preferred embodiment of the present invention. Other electrode tip designs that provide field enhancement through provision of energy director locations of reduced area will be apparent to those skilled in the art, and these are included in the spirit of the invention. Examples of other electrode tips that provide field enhancement are shown in FIGS. 45–53, FIG. 45 shows a ridge 598 configured in the shape of a helix. FIG. 46 shows the helix of FIG. 45 with grooves 600 further reducing the energy director area. FIG. 47 illustrates narrow extensions 602 that provide field enhancement by causing field concentration on the bottom 2 or 3 extensions in contact with the tissue. FIG. 48 is a series of independent, non-connected disks 604 threaded on the straight portion of wire 606. FIG. 49A shows independent disks 608 on a conductor 610 of curved shape. The roller loop electrode of FIG. 49A is an example of the flexible use of disks to create an electrode tip. A wide range of loop shapes are possible to form a "custom" electrode shape for a particular purpose. Examples of custom shapes are shown in FIGS. 49B, C and D. As in the other figures, the two leads, such as 611 and 613 of FIG. 49B are preferably connected, resulting in a more mechanically supported structure. Application of RF energy to either or both of leads 611 and/or 613 will empower the electrode. Combination of these or similar electrodes with each other, or with other types of electrodes in either monopolar or bipolar arrangements are all included in the spirit of the present invention. FIG. 50 illustrates forming reduced area energy directors 612 from a cylindrical shaped roller or helical profile roller.

Although the roller feature has advantages as discussed above in reference to FIG. 44, combined vaporization and coagulation can be achieved with non-rotating electrode tips. Electrode configurations that are non-rotating, but incorporate the RF field enhancement feature are also included in the spirit of the present invention. For example, FIG. 51 shows an electrode configuration that is inherently non-rotating, but can be fabricated with surfaces of the appropriate area formed as turns 614 of the conductor 616. Other examples of non-rotating vaporization tips would be structures such as the rollers of the various figures described above if the rollers were soldered or otherwise attached in a non-rotating manner. And, of course, a flat plate configuration with V shaped grooves or other profile on the bottom could be designed to vaporize tissue. These various alternative designs are all included in the spirit of the present invention.

FIG. 52 illustrates a further alternate embodiment wherein the electrode has two roller electrodes 618, 620, however the electrodes can be of any type, such as those discussed above in the various figures. Since the RF voltage to each tip 618, 620 is substantially the same, the area of vaporization is approximately doubled. Since the electrode's energy director tips are arranged in staggered fashion, as the electrode is moved, an area is vaporized and coagulated by one tip and then vaporized and coagulated again by the other.

FIG. 53 shows an embodiment of the present invention using two tips in monopolar mode wherein a first electrode tip 622 in the shape of a single wire loop is operated in combination with a second tip 624 having a larger surface area. The very limited small area of the wire tip 622 provides an intense field pattern, resulting in a high power density that cuts tissue. The sharp cutting action, however, leaves the tissue exposed and bleeding. The function of the second tip 624 is to follow the first tip 622 and coagulate the exposed tissue. A coagulating tip has surface area(s) that are larger than those configured for vaporization. Specific dimensions for the tips can vary depending on the desired tissue effect. The differences in tip surface construction between a tip designed for coagulation and one designed for vaporization can be readily determined through experiment by one skilled in the art, as may be necessary in the designs where the quantitative difference is not obvious from the disclosure of the present invention. Such a case, for example, would be a coiled electrode tip where the wire diameter and spacing would determine whether the tip cuts or vaporizes or does both simultaneously. The coil shown for tip 614 of FIG. 51 if designed for coagulation would therefore have larger dimensions than a similar coil for vaporization, the dimensions including wire diameter, spacing, etc., resulting in the required larger area. The combination of a cutting loop electrode tip followed by a coagulating tip is a novel feature of the present invention.

Other combinations of tips in a monopolar mode will be apparent from the above disclosure to those skilled in the art, and they are also included in the spirit of the present invention. Various other monopolar embodiments will be described in reference to the following figures of the drawing.

Alternative embodiments of the present invention also include bipolar operation, where the electrode (or electrodes) receiving RF of one polarity (exp. active) are spaced more closely to the electrode (or electrodes) of the opposite polarity (return) than is the case in monopolar operation. In monopolar operation, the return electrode is a conductor of large surface area attached to the patient's body exterior, and serves as a "return electrode" from the active electrode. Any of the above electrode tips discussed in relation to monopolar operation can also be used in bipolar operation, an example being shown in FIG. 54 wherein a side view is given of two electrodes 626, 628 with roller tips 630, 632. One of the electrodes, for example, 626 is connected to the active side of the RF power supply and the other 628 is connected to the return side. An advantage of using the bipolar configuration is that the close spacing of the two electrodes confines the RF power to a smaller area of tissue. Instead of the RF fields spreading outward and terminating/returning through a body plate, the field is confined between the two electrodes as illustrated in FIG. 54, where the electric field pattern is predominantly as shown by the dashed lines 634 passing through the tissue 636 near the surface 638. The higher conductivity of the tissue 636 tends to confine the RF fields primarily in the tissue 636. The two electrodes can be attached mechanically as at 640, or in other ways known to those skilled in the art, or they can be mechanically independent enabling connection to the proximal connector of the device.

Other bipolar arrangements are shown in FIGS. 55–60. FIG. 55 shows two coils of wire interwound and spaced apart with insulative material 642 such as ceramic. As an example of operation, first coil 644 could be connected to the active side of an RF supply, and the second coil 646 (insulated from the first coil) would be connected to the return side of the RF supply. The present invention also includes configurations wherein the two electrodes are not of the same configuration. This is illustrated somewhat schematically in FIG. 56 where one tip 648 is a thin wire loop, and the other tip 650 is a roller bar. In this case, for example, the thin loop could be used for cutting, and the roller bar could be designed for either coagulation, or simultaneous vaporization and coagulation, depending on the design of the roller surface as explained above. FIG. 57A is an arrangement of a thin wire loop electrode 652 for cutting, which could, for example, be connected to the active RF supply side, and a thicker loop electrode 654 for coagulation which would be connected to the return RF supply side. FIGS. 57B–57E show various electrode cross sections, such as noted by cross section designations "AA" and "BB" in FIG. 57A. In FIG. 57A, either of the electrodes 652 and/or 654 could be of any desired cross section, such as the triangular shape in FIG. 57B, the flat shape of FIG. 57C, or round or rectangular/square in FIGS. 57D and 57E respectively. Other cross sections are also included in the spirit of the invention. In addition, the cross section of FIGS. 57B–57E and other cross sections apply to the other wire electrodes in this specification, such as those in FIGS. 39, 51, 56 and 59.

FIG. 58 shows two loop shaped electrodes 656 and 658, each of which has a plurality of narrow edged roller disks 660, each disk independently free to rotate on the associated wire loop 662. The narrow edged roller disk electrodes 656, 658 are suitable for vaporization-coagulation effect.

FIG. 59 illustrates the use of two cutting loop electrodes 664, 666 and FIG. 60 shows a combination of a roller disk electrode 668 for vaporization and a roller electrode with a plain surface 670 for coagulation.

FIG. 61 is an example of an integrated bipolar electrode using roller disks. Conductor 672 is for connection to one side (active or passive) of the RF supply, and conductor 674 is for connection to the opposite (passive or active) side. Conductor 672 joins arms 676, 678 which support coaxially aligned tubes 680, 682 upon which are rotatably mounted disks 684, 686.

Insulative tubes 688, 690 are installed inside tubes 680, 682, through which passes conductor 692 joined to conductor branches 694, 696 further joined to conductor 674. The insulative tubes 688, 690 have insulative flanges 698, 700 for the purpose of electrically isolating roller disk 702 from conductor tubes 680, 682. Disk 702 is rotatably mounted on conductor 692. In operation, energy passes between disk 702 at one RF polarity to disks 684, 686 at the other polarity, heating tissue lying within the electromagnetic field formed therebetween.

In addition to the above combinations of electrodes in bipolar and monopolar modes, other combinations will be apparent from the above disclosure to those skilled in the art, and they are to be included in the spirit of the present invention.

The various electrode combinations discussed above in relation to the figures in description of the bipolar mode can also be used, in monopolar mode simply by connecting both electrode's proximal connectors, such as 667 and 669 in FIG. 60, to the same side (active side) of the RF supply, or by connecting the conductor branches leading to the tips together, as in FIG. 52, and connecting the resultant single conductor to the RF supply. As described above, in monopolar mode, the return path (return electrode) is through a conductive surface adjacent/attached to the patient's exterior body surface with a conductor leading from there to the RF supply. All of these combinations are included in the present invention.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. An RF electrode device comprising:
   (a) electrode tip module means including first tip means for conducting RF energy to body tissue;
   (b) electrode stem means including
      i) first conductor means for electrically connecting said first tip means at a distal end of said first conductor means to a first connective means at a proximal end of said first conductor means for connection to a first side of a source of RF energy;
      ii) insulative means for electrically insulating a portion of said first conductor means;
      iii) telescope guide means for guiding an endoscopic telescope, said guide means constructed of electrically insulative material.

2. An RF electrode device as recited in claim 1 wherein said telescope guide means has a saddle shape.

3. An RF electrode device as recited in claim 1 wherein said first tip means is a wire loop.

4. An RF electrode device as recited in claim 1 wherein
   (a) said electrode tip module means includes a second tip means for receiving energy from said body tissue; and
   (b) said electrode stem means further includes
      (i) second conductor means for electrically connecting said second tip means at a distal end of said second conductor to a second conductive means at a proximal end of said first conductor means for connecting to a second side of said source of RF energy; and
      (ii) insulative means for electrically insulating a portion of said second conductor means.

5. An RF electrode device as recited in claim 4 wherein said electrode stem means further includes
   (i) second conductor means for electrically connecting said second tip means at a distal end of said second conductor means to a second connective means at said proximal end of said second conductor means for connection to a second side at a source of RF energy; and
   (ii) wherein said insulative means further insulates a portion of said second conductor means.

6. An RF electrode device as recited in claim 1 wherein said first tip means is a needle.

7. An RF electrode device as recited in claim 1 wherein said first tip means is a roller.

8. An RF electrode device as recited in claim 7 wherein said roller has extremities of smaller area providing RF field enhancement.

9. An RF electrode device as recited in claim 7 further comprising connecting means for removably connecting said electrode tip module means from said electrode stem means.

10. A method of operating an endoscopic surgical instrument for tissue treatment by application of RF energy comprising:

(a) depositing an electrically conductive fluid on a body tissue;

(b) applying an active side of an RF energy source to an electrode tip for contact with said tissue and said fluid at a first position; and (c) receiving RF energy passed through said tissue and said fluid to a second position for return to a passive side of said RF energy source.

11. A method as recited in claim 10 wherein said conductive fluid is a saline solution.

12. A method as recited in claim 10 wherein said receiving includes conduction of said RF energy through a portion of a housing of said endoscopic surgical instrument.

13. A method as recited in claim 10 wherein said applying is performed by conduction of said RF energy to said tissue and fluid through a first RF electrode tip, and said receiving includes conduction of said RF energy through a second RF electrode tip.

14. A method as recited in claim 10 wherein said receiving includes conduction of said RF energy through a conductive pad on an exterior portion of a patient's body.

15. An endoscopic surgical instrument comprising:

(a) an endoscope housing having an elongated housing means for insertion into a body cavity, said housing means having a conduit formed therethrough;

(b) an RF electrode device for installation through said conduit including
  (i) electrode tip module means including first tip means for conducting RF energy to body tissue;
  (ii) electrode stem means including
    a) first conductor means for electrically connecting said first tip means at a distal end of said first conductor means to a first connective means at a proximal end of said first conductor means for connection to a first side of a source of RF energy; and
    b) insulative means for electrically insulating a portion of said first conductor means.

16. An endoscopic surgical instrument as recited in claim 15 further comprising:

(a) conductive element means having second connection means for electrically connecting said conductive element means to a second side of said source of RF energy;

whereby said endoscopic surgical instrument is operable upon connection to said RF energy source to cause RF energy to pass between said first tip means and said conductive element means.

17. An endoscope surgical instrument as recited in claim 16 wherein said conductive element is a conductive pad means for attachment to an exterior body portion of a patient to be treated;

whereby said endoscopic surgical instrument is operable in a monopolar mode wherein RF energy from said RF energy source can pass between said tip means and said conductive pad means.

18. An endoscopic surgical instrument as recited in claim 17 further comprising fluid supply means for directing a fluid through said conduit and out said distal end of said conduit.

19. An endoscopic surgical instrument as recited in claim 18 wherein said fluid is non-isotonic.

20. An endoscopic surgical instrument as recited in claim 18 wherein said fluid is isotonic for enhancing electrical current between said first tip means and said conductive element.

21. An endoscopic surgical instrument as recited in claim 16 wherein said conductive element is a conductive means included as part of said elongated housing means;

whereby said endoscopic surgical instrument is operable upon connection to said RF energy source to cause RF energy to pass between said first tip means and said conductive means and thereby operate in a bipolar mode.

22. An endoscopic surgical instrument as recited in claim 21 further comprising fluid supply means for directing a fluid through said conduit and out said distal end of said conduit.

23. An endoscopic surgical instrument as recited in claim 22 wherein said fluid is non-isotonic.

24. An endoscopic surgical instrument as recited in claim 22 wherein said fluid is isotonic for enhancing electrical current between said first tip means and said conductive element.

25. An endoscopic surgical instrument as recited in claim 16 wherein said conductive element is a second tip means for extension from a distal end of said conduit;

whereby said endoscopic surgical instrument is operable upon connection to said RF energy source to cause RF to pass between said first tip means to said second tip means and thereby operate in a bipolar mode to treat a localized are of tissue.

26. An endoscopic instrument as recited in claim 25 further comprising fluid supply means for directing a fluid through said conduit and out said distal end of said conduit.

27. An endoscopic instrument as recited in claim 26 wherein said fluid is non-isotonic.

28. An endoscopic instrument as recited in claim 26 wherein said fluid is isotonic for enhancing electrical current between said first tip means and said second tip means.

* * * * *